(12) United States Patent
Pak et al.

(10) Patent No.: US 11,311,305 B2
(45) Date of Patent: *Apr. 26, 2022

(54) SURGICAL INSTRUMENTS WITH COUPLING MEMBERS TO EFFECT MULTIPLE PIVOT AXES

(71) Applicant: Arculant, Inc., Santa Clara, CA (US)

(72) Inventors: Jimmy Joung Pak, Moraga, CA (US); Mark Andrew Spencer, Santa Clara, CA (US)

(73) Assignee: Arculant, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/183,334

(22) Filed: Feb. 23, 2021

(65) Prior Publication Data
US 2021/0196300 A1 Jul. 1, 2021

Related U.S. Application Data

(63) Continuation of application No. 16/820,518, filed on Mar. 16, 2020.
(Continued)

(51) Int. Cl.
*A61B 17/28* (2006.01)
*A61B 17/30* (2006.01)
(Continued)

(52) U.S. Cl.
CPC .......... *A61B 17/2816* (2013.01); *A61B 17/30* (2013.01); *A61B 2017/00477* (2013.01); *B25B 9/02* (2013.01)

(58) Field of Classification Search
CPC . A61B 17/2812; A61B 17/2816; A61B 17/30; A61B 2018/1462; B25B 9/00; B25B 9/02
See application file for complete search history.

(56) References Cited

U.S. PATENT DOCUMENTS 561,176 A 6/1896 Parker
1,004,871 A 10/1911 Gundorph
(Continued)

FOREIGN PATENT DOCUMENTS

DE 3640471 C2 6/1988
DE 10155585 A1 6/2003
(Continued)

OTHER PUBLICATIONS

Sklar Instruments, Sklar Hospital Catalog, 2014, Entire Catalog (see e.g., pp. 17-137, 166-178, 182-183, 206-207, 235-256, 260-274, 298-299, 320-321, 345-348, 360-361, 370-381, 383-384, 392-393, 399-402, 407-409, 418-420, 460-464, 475-487, 492-535, 603-605, 638-649, among other pages), West Chester, PA, U.S.A.
(Continued)

*Primary Examiner* — Sarah W Aleman
(74) *Attorney, Agent, or Firm* — Kokka & Backus, PC

(57) ABSTRACT

Various embodiments relate generally to surgical instruments, tools, and apparatuses for medical use, including, but not limited to, forceps, tweezers, and pincers, as well as other anatomical tools for surgical and medical uses, and, more specifically, to surgical instruments implementing a coupling member to effectuate multiple pivot axes enhance, for example, effective lengths with which to access an internal surgical site. In some examples, a surgical instrument may include lever members, each of which may include a pivot portion, a force application portion, and a contacting portion. The surgical instrument may also include a coupling member configured to position multiple pivot portions adjacent proximal ends of a first and second lever member to effectuate a closing state at which contacting portions are positioned at a second distance, which is less than the first distance, at distal ends of a first and second lever member.

20 Claims, 20 Drawing Sheets

Related U.S. Application Data

(60) Provisional application No. 62/819,637, filed on Mar. 17, 2019.

(51) Int. Cl.
*B25B 9/02* (2006.01)
*A61B 17/00* (2006.01)

(56) References Cited

U.S. PATENT DOCUMENTS

| | | | |
|---|---|---|---|
| 1,095,564 A | | 5/1914 | Engelsman |
| 1,356,048 A | | 10/1920 | Dederer |
| 1,701,995 A | | 2/1929 | Anderson |
| 2,406,393 A | | 8/1946 | Neugass |
| 2,412,255 A | | 12/1946 | Ferguson |
| 2,595,683 A | | 5/1952 | Lo Monte |
| 2,618,268 A | | 11/1952 | English |
| 2,743,726 A | | 5/1956 | Grieshaber |
| 2,943,521 A | | 7/1960 | Betton |
| 3,209,753 A | | 10/1965 | Hawkins et al. |
| 3,265,068 A | * | 8/1966 | Holohan ............... A61B 17/30 606/210 |
| 3,367,336 A | * | 2/1968 | Eizenberg ............ A61B 17/30 606/210 |
| 3,417,752 A | | 12/1968 | Butler |
| 3,446,211 A | | 5/1969 | Markham |
| 3,515,139 A | | 6/1970 | Mallina |
| 3,653,389 A | | 4/1972 | Shannon |
| 3,815,609 A | * | 6/1974 | Chester ............... A61B 17/30 606/210 |
| 3,892,435 A | | 7/1975 | Huey |
| 4,020,846 A | | 5/1977 | Stokes |
| 4,212,305 A | * | 7/1980 | Lahay ............... A61B 17/30 294/99.2 |
| 4,318,313 A | | 3/1982 | Tartaglia |
| 4,325,376 A | | 4/1982 | Klieman et al. |
| 4,461,297 A | | 7/1984 | Sutter |
| 4,475,544 A | | 10/1984 | Reis |
| 4,761,028 A | * | 8/1988 | Dulebohn ............ A61B 17/30 294/99.2 |
| 5,176,702 A | | 1/1993 | Bales et al. |
| D357,846 S | * | 5/1995 | McNaughton ............... D7/686 |
| 5,578,032 A | | 11/1996 | Lalonde |
| 5,607,451 A | | 3/1997 | Menocal, Jr. |
| D449,374 S | * | 10/2001 | Campbell .................. 23/411 |
| D456,077 S | | 4/2002 | Etter et al. |
| 6,749,610 B2 | | 6/2004 | Kirwan, Jr. et al. |
| D532,932 S | * | 11/2006 | Shih ........................ D28/55 |
| D559,458 S | | 1/2008 | Garland et al. |
| 8,679,140 B2 | | 3/2014 | Butcher |
| D717,002 S | * | 11/2014 | Johnston .................. D28/55 |
| 2002/0082596 A1 | | 6/2002 | Buysse et al. |
| 2005/0125013 A1 | * | 6/2005 | Kessler ............... A61B 17/30 606/148 |
| 2007/0167977 A1 | | 7/2007 | Biolchini |
| 2009/0179442 A1 | | 7/2009 | Mithal et al. |
| 2010/0298865 A1 | * | 11/2010 | Aufaure .............. A61B 17/30 606/210 |
| 2014/0046363 A1 | | 2/2014 | Rönnow |
| 2017/0312013 A1 | * | 11/2017 | Scheller ............ A61B 18/1442 |
| 2018/0168568 A1 | | 6/2018 | Ali et al. |
| 2020/0222071 A1 | | 7/2020 | Pak et al. |
| 2020/0289138 A1 | | 9/2020 | Pak et al. |

FOREIGN PATENT DOCUMENTS

| | | |
|---|---|---|
| EP | 3897412 A1 | 10/2021 |
| EP | 3941368 | 1/2022 |
| FR | 2644056 A1 | 9/1990 |
| JP | 201029507 A | 2/2010 |
| WO | 1990003763 A1 | 4/1990 |
| WO | 2015041394 A1 | 3/2015 |
| WO | 2020132321 A1 | 6/2020 |
| WO | 2020190972 A1 | 9/2020 |

OTHER PUBLICATIONS

Young, Lee, Notification of Transmittal of the International Search Report and the Written Opinion of the International Searching Authority, or the Declaration, dated May 14, 2020 for International Application No. PCT/US2019/067605.

Young, Lee, Notification of Transmittal of the International Search Report and the Written Opinion of the International Searching Authority, or the Declaration, dated Jul. 1, 2020 for International Application No. PCT/US2020/023209.

Aleman, Sarah W., Final Office Action dated Dec. 21, 2021 for U.S. Appl. No. 16/820,518.

Aleman, Sarah W., Non-Final Office Action dated May 17, 2021 for U.S. Appl. No. 16/820,518.

* cited by examiner

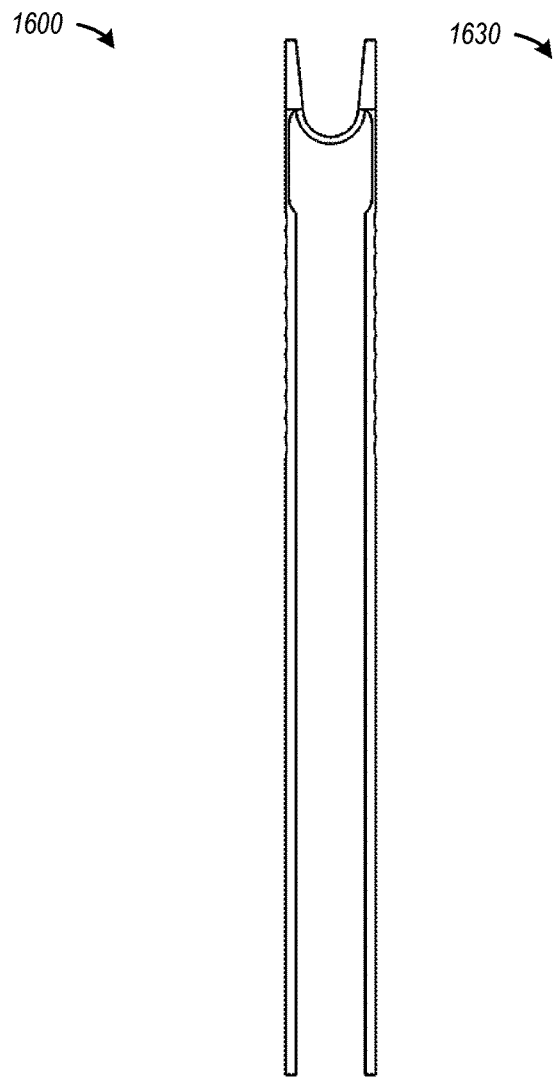
FIG. 16A
FIG. 16B
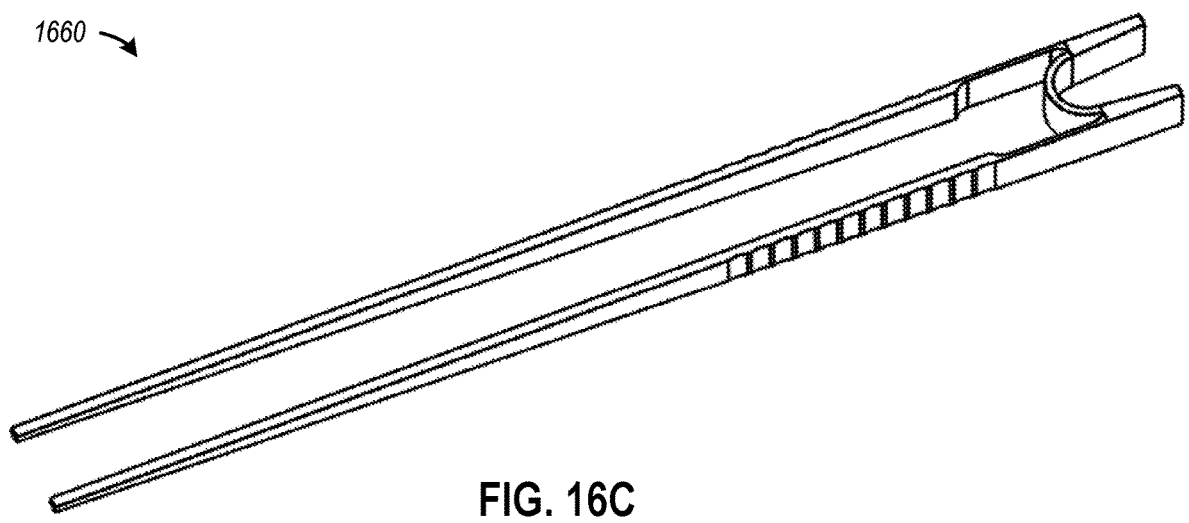
FIG. 16C

SURGICAL INSTRUMENTS WITH COUPLING MEMBERS TO EFFECT MULTIPLE PIVOT AXES

CROSS-REFERENCE TO APPLICATIONS

This application is a continuation application of U.S. patent application Ser. No. 16/820,518 filed on Mar. 16, 2020 and titled "Surgical Instruments with Coupling Members to Effect Multiple Pivot Axes;" U.S. patent application Ser. No. 16/820,518 claims the benefit of U.S. Provisional Patent Application No. 62/819,637 filed on Mar. 17, 2019 and titled "Advanced Surgical Forceps," all of which are herein incorporated by reference in their entirety for all purposes.

FIELD

Various embodiments relate generally to surgical instruments, tools, and apparatuses for medical use, including, but not limited to, forceps, tweezers, and pincers, as well as other anatomical tools for surgical and medical uses, and, more specifically, to surgical instruments implementing a coupling member to effectuate multiple pivot axes that enhance, for example, effective lengths with which to access an internal surgical site and application of force to facilitate grasping and manipulation of tissues associated with surgery.

BACKGROUND

Surgeons and medical professionals are increasingly required to improve productivity with an aim to maintain or reduce healthcare costs, including costs related to operating rooms and surgeries. Some traditional surgical tools hinder the goals of improving productivity as some surgical tools may implement suboptimal designs and configurations that have not changed in decades. For example, suboptimal designs and configurations can cause fatigue unnecessarily, and can provide for less than optimal useable length of the tool to accomplish the tool's function. One class of surgical tools susceptible to impeding improved productivity includes conventional forceps that employ a fixed hinge mechanism. These traditional forceps have several drawbacks.

FIG. 1A is a diagram 100 showing a perspective view of conventional surgical forceps 101 that has fulcrum assembly 103 as a flat, fixed hinge connected to each shank 101a and 101b to enable tips of forceps 101 in grip region 106 to grip any number of anatomical items, such as tissues, organs (e.g., bowels), arteries, veins, bones, etc. Structures of conventional surgical forceps 101 can be described relative to a lateral plane 110, a longitudinal plane 112, and a bisecting plane 114. As shown, longitudinal plane 112 includes a pivot axis 104 about which shanks 101a and 101b rotate, and substantially divides surgical forceps 101 into two halves, whereby one half includes shank 101a and the other half includes shank 101b. Lateral plane 110 is orthogonal to longitudinal plane 112 and substantially divides each of shanks 101a and 101b into symmetrical halves along, for example, plane-intersection lines 107a and 107b. Bisecting plane 114 divides a length 108 of forceps 101 from point 102a to point 102b in half, and is orthogonal to both lateral plane 110 and longitudinal plane 112. Bisecting axis 114a is a line at which bisecting plane 114 intersects longitudinal plane 112. Finger engagement region 105, which typically extends through bisecting plane 114, includes a surface at which a finger or thumb may engage forceps 101 to grasp an object, such as tissue.

FIG. 1B is a diagram 120 as a side view of conventional surgical forceps 121 in an open state. Forceps 121 include a fulcrum assembly 123 at one end and tips 122b1 and 122b2 in a grip region 126 at the other end. Typically, fulcrum assembly 123 is a flat, fixed hinge connected to a shank 121a and a shank 121b, and provides a pivot axis 124 about which each of shanks 121a and 121b rotate. Usually, fulcrum assembly 123 is formed by welding shanks 121a and 121b to each other to form a flat hinge that is non-locking and without a pivot assembly (e.g., a rivet or pin typically used to provide 'scissoring'-like functionality). As a result, flat material within fulcrum length 128a reduces the potential use of forceps length 128. Further, finger engagement region 125 is usually disposed at and over bisecting plane, and thus is typically designed for surgeons to grasp forceps 121 at the middle of length 128, which, in turn, usually reduces a useful working length between a surgeon's fingers on forceps 121 and tips 122b1 and 122b2. Note that in an initially closed state, forceps 121 are commonly in a "bowed" shape in which distances 129 between one of shanks 121a and 121b and a longitudinal plane 132 are present when tips 122b1 and 122b2 are in contact.

Yet another drawback to conventional forceps 121 is that a relatively small or limited range of motion provided by a "pinch distance" 131, in turn, limits a force that can cause tips 122b1 and 122b2 to transfer the force to grasp an object. In typical usage, pinch distance 131 decreases to about a zero distance when a maximal force is applied. Hence, a limitation usually arises as a thumb and a pad of an index finger (e.g., of a surgeon) causes pinch distance 131 to decrease from, for example, about 4 mm to about 0 mm, which may be a limited range of motion with which to apply a force for transference to tips 122b1 and 122b2. As such, a maximal force is typically reached at pinch distance 131 of about 0 mm, which, in turn, causes shanks 121a and 121b to contact each other along their longitudinal length from point 102a to point 102b of FIG. 1A (e.g., in a "flattened" configuration). Once the limited range of motion associated with pinch distance 131 is depleted for forceps 121, any additional forces applied to forceps 121 do not transfer generally to tips 122b1 and 122b2.

FIG. 1C is a diagram 140 showing a side view of conventional surgical forceps 141 in a closed state. As shown, a longitudinal plane 152 passes through a fulcrum assembly 143, a pivot axis 144, and engaged tips 142b. An applied force 156 is shown to be applied to a surface of a finger engagement region 145 to maintain forceps 141 in a closed state. Applied force 156 is of at least an amount to overcome a spring force 158 that naturally causes forceps 141 to return to an open state. In event forceps 141 are used to lift an object (e.g., tissue), a lift force 154a may be applied to a common surface portion at which applied force 156 is exerted. During a lifting event, friction force 157 may be applied to a textured surface on shanks 121a and 121b to enhance a surgeon's grip. In a closed state, a geometry 153 formed to include pivot axis 144 and surface portions of finger engagement region 145 is such that a direction of a lift force 154a (e.g., parallel to longitudinal plane 152) that omits a structure of forceps 141. Further, a point at which application of applied force 156 is applied usually defines a useful length 155 with which a surgeon or medical professional may effectively use forceps 141 to grasp tissue.

Forceps 141 may be Debakey forceps and may be 12 inches in length extending from end 191a to tips 142b.

Forces exerted at or about bisecting plane 194 increasing from approximately 4 Newtons to approximately 18 Newtons may generate approximately 0 megapascals ("MPa") to approximately 0.25 MPa of pressure at tips 142b. However, forces exerted at or about bisecting plane 194 increasing from approximately 18 Newtons to approximately 32 Newtons may yield decreasing amounts of pressure (e.g., from about 0.25 MPa to about 0 MPa). By contrast, forces exerted at or about $\frac{2}{3}^{rd}$ distance 192 from tips 142b ranging from approximately 4 Newtons to approximately 9 Newtons may generate approximately 0.2 megapascals ("MPa") to approximately 0.4 MPa of pressure at tips 142b. However, forces exerted at or about $\frac{2}{3}^{rd}$ distance 192 (e.g., 66.7% of 12 inches) increasing from approximately 9 Newtons to approximately 32 Newtons may yield decreasing amounts of pressure (e.g., from about 0.4 MPa to about 0.2 MPa). Thus, in the example shown, maximum amounts of pressure are about 0.25 MPa and 0.4 MPa for forces exerted at or about bisecting plane 194 and $\frac{2}{3}^{rd}$ distance 192, respectively.

FIG. 2 is a diagram 200 depicting a typical approach to using conventional surgical forceps with traditional design configurations. As shown, a subject 210 undergoing surgery may require any number of surgical tools, forceps 201a, 201b, and 201c or any other tool, such as clamping tools 242, 244, 246, etc., at an internal surgical site 212. A cover 230, such as a surgical drape, towel, pad, etc., may define a size of an opening of internal surgical site 212. Also, clamping tools 242, 244, 246 may be disposed on a cover 230 and may extend upward from subject 210, thereby obstructing a use of forceps 201a. These tools, including forceps 201a, 201b, and 201c, may be required to access tissue or objects at a depth 229. Inset 290 depicts a hand 236a of a first surgeon using a "pencil grip" to hold forceps 201a at finger engagement region 245. Commonly, other surgeons may also vie to gain access to internal surgical site 212 during a surgery. For example, consider two additional surgeons are participating in the surgery. A hand 236b of a second surgeon is holding forceps 201b, as shown within inset 292. A hand 236c of a third surgeon is holding forceps 201c, as shown within inset 294. Drawbacks to conventional forceps 201a, 201b, and 201c include reduced useful lengths 255a, 255b, and 255c with which surgeons may use to avoid each other's tools, clamps 242 to 246, or any other obstacle when accessing anatomical objects at depth 229. Reduced useful lengths 255a, 255b, and 255c typically requires more coordination and stresses to successfully grasp and hold objects to ensure a successful result for subject 210.

Thus, what is needed is a solution for facilitating implementation of surgical tools without the limitations of conventional techniques.

BRIEF DESCRIPTION OF THE DRAWINGS

Various embodiments or examples ("examples") of the invention are disclosed in the following detailed description and the accompanying drawings:

FIGS. 16A, 16B, and 16C depict a front view, a side view, and an perspective view, respectively, of another example of a surgical instrument, according to various examples.

DETAILED DESCRIPTION

Various embodiments or examples may be implemented in numerous ways, including as a system, a process, an apparatus, a user interface, or a series of program instructions on a computer readable medium such as a computer readable storage medium or a computer network where the program instructions are sent over optical, electronic, or wireless communication links. In general, operations of disclosed processes may be performed in an arbitrary order, unless otherwise provided in the claims.

A detailed description of one or more examples is provided below along with accompanying figures. The detailed description is provided in connection with such examples, but is not limited to any particular example. The scope is limited only by the claims, and numerous alternatives, modifications, and equivalents thereof. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1A:
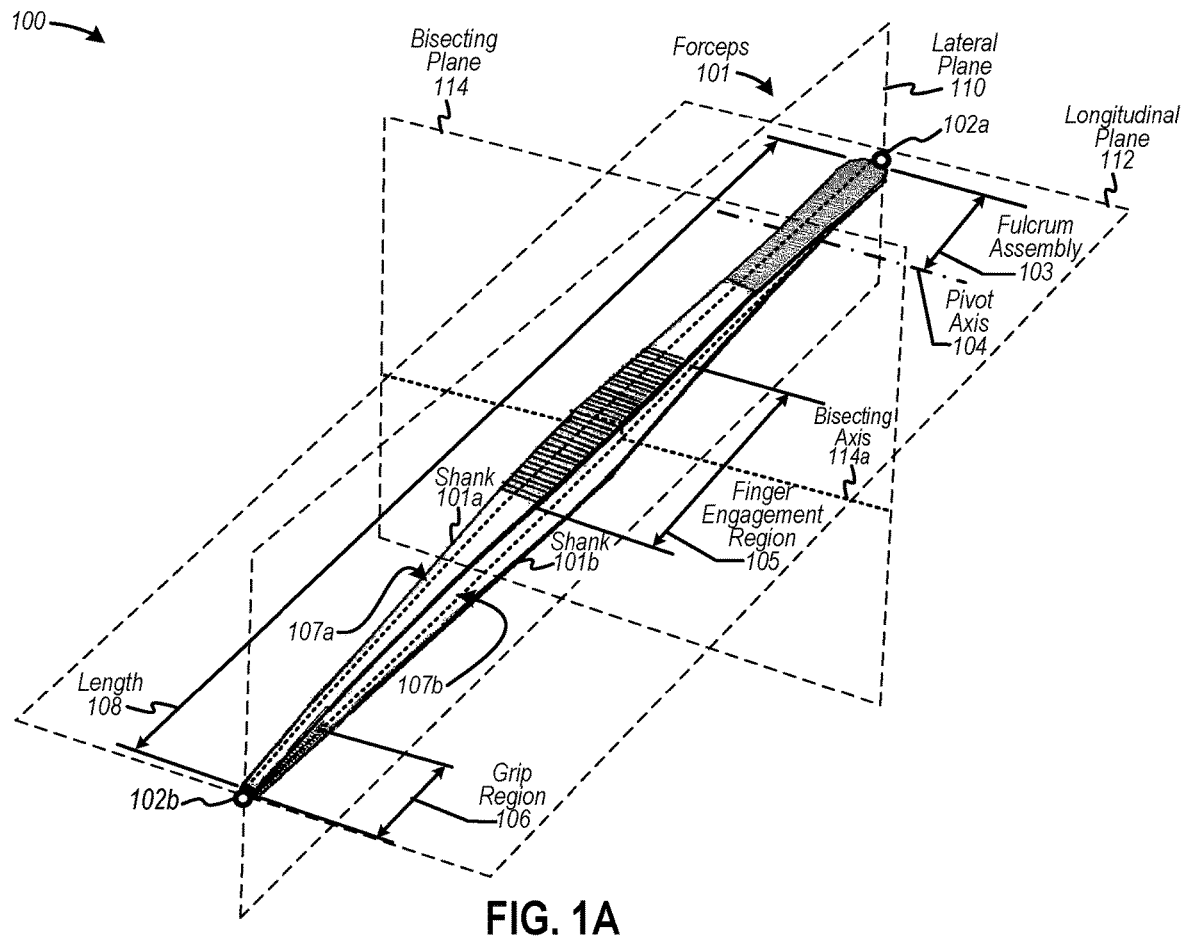
FIG. 1A is a diagram showing a perspective view of conventional surgical forceps that has a fulcrum assembly.
Figure 1B:
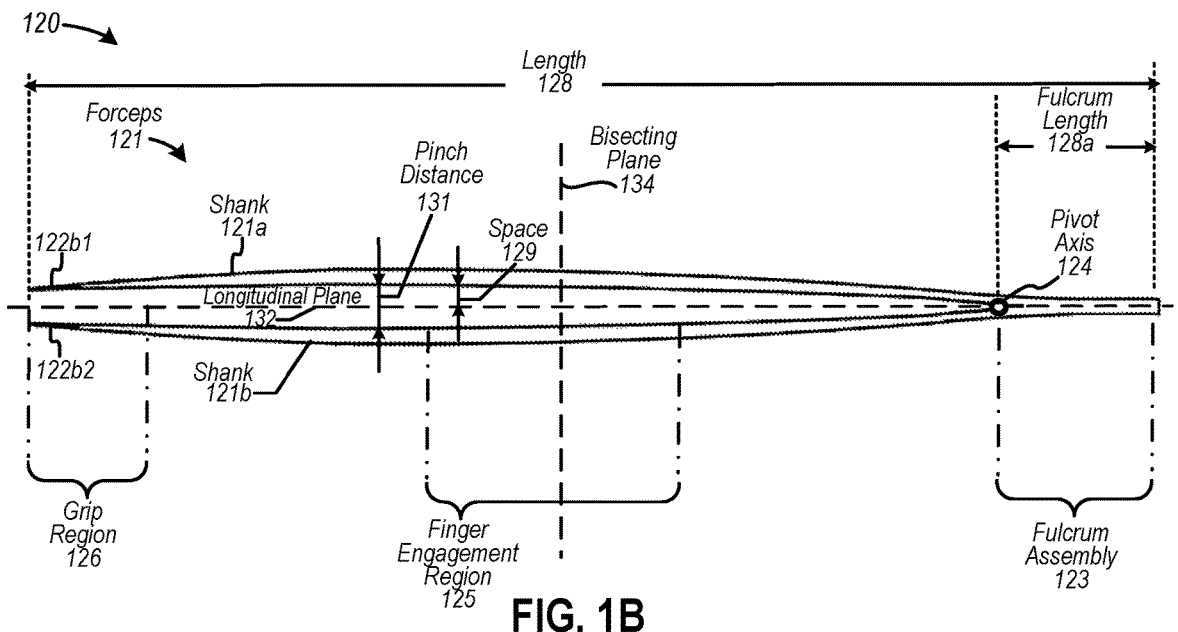
FIG. 1B is a diagram as a side view of conventional surgical forceps in an open state.
Figure 1C:
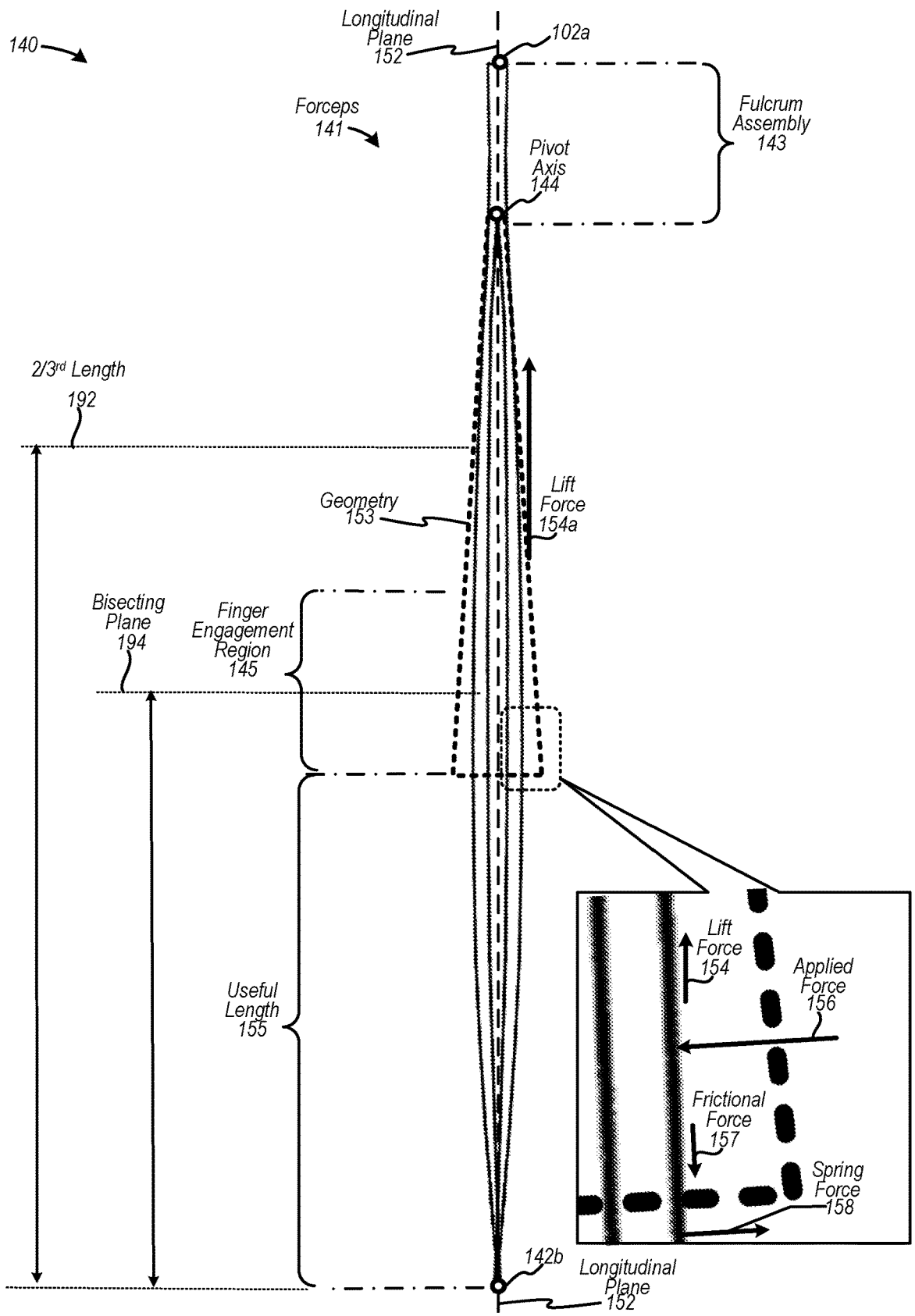
FIG. 1C is a diagram showing a side view of conventional surgical forceps in a closed state.
Figure 2:
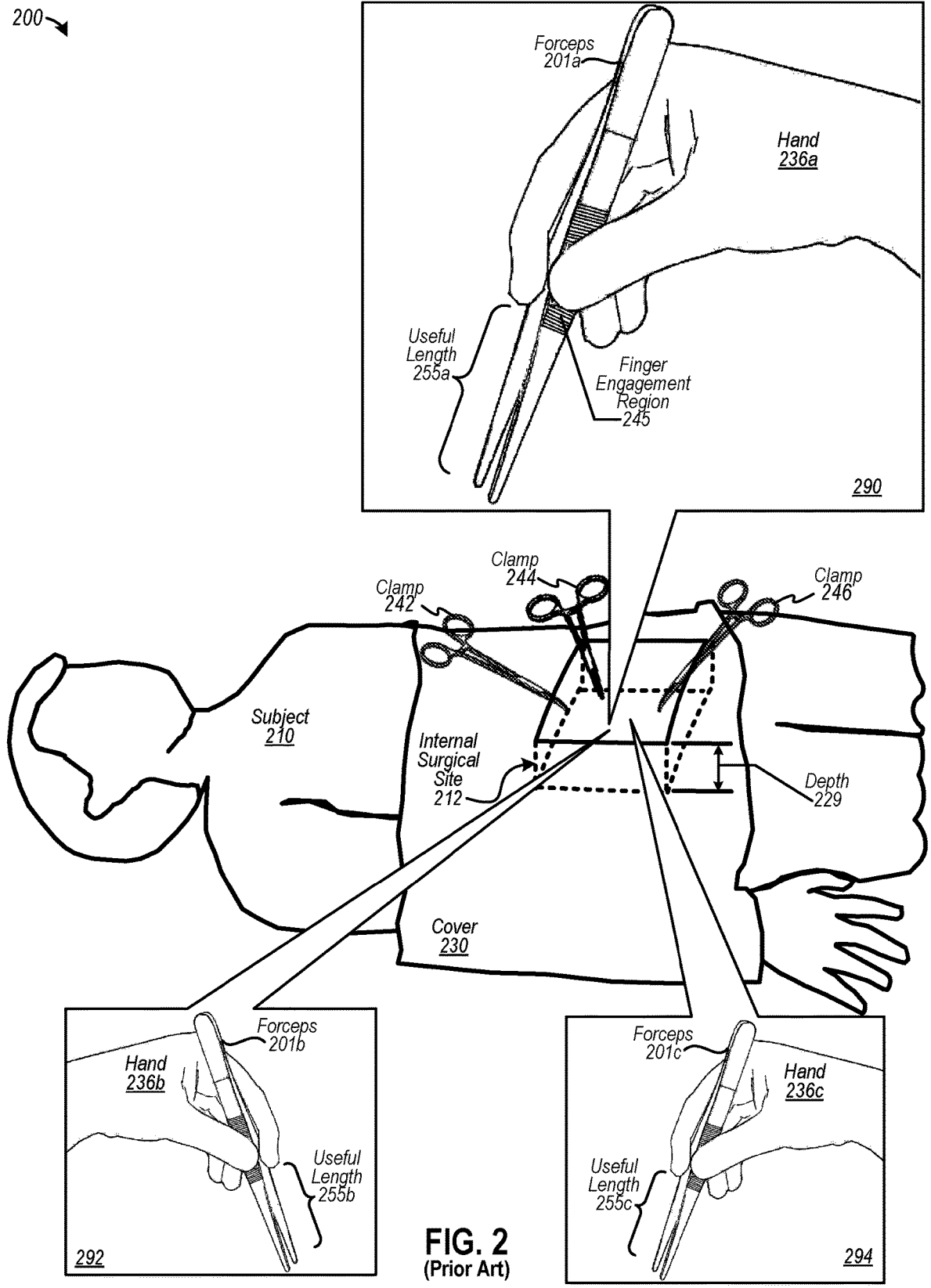
FIG. 2 is a diagram depicting a typical approach to using conventional surgical forceps with traditional design configurations.
Figure 3:
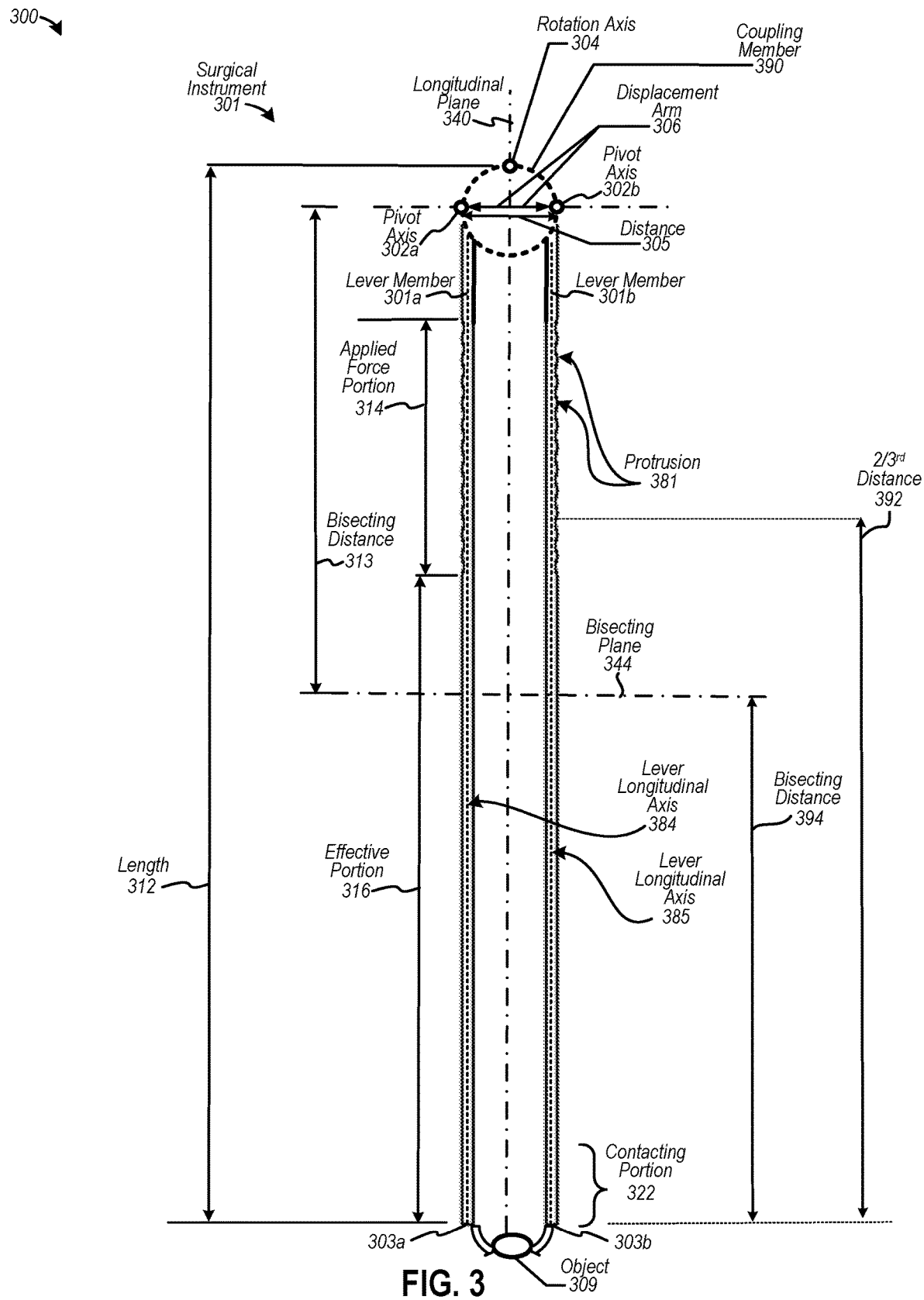
FIG. 3 is a diagram depicting an example of a surgical instrument implementing a coupling member including multiple pivot axes, according to some embodiments.

FIG. 3 is a diagram depicting an example of a surgical instrument implementing a coupling member including multiple pivot axes, according to some embodiments. Diagram 300 depicts a surgical instrument 301 including a coupling member 390 to, among other things, implement multiple pivot axes, such as a pivot axis 302a and a pivot axis 302b. Coupling member 390 may be configured to couple to a lever member 301a at or adjacent to pivot axis 302a, and may be further configured to couple to a lever member 301b at or adjacent to pivot axis 302b. As shown, one or more of lever member 301a and lever member 301b each may include an applied force portion 314, an effective portion 316, and a contacting portion 322, which may include ends 303a and 303b. In some cases, ends 303a and 303b may be disposed distally, as distal ends, relative to pivot axes 302a and 302b, as well as a rotation axis 304, each of which may be disposed at another end (e.g., at a proximal end). In the example shown, surgical is 301 and lever members 301a and 301b is depicted as being in an open state (e.g., absence of applied forces to applied force portion 314). In operation, under applied forces, lever members 301a and 301b rotate relative to pivot axes 302a and 302b, respectively, and ends 303a and 303b of surgical instrument may rotate relative to rotation axis 304, which may be positioned in various positions within coupling member 390.

Applied force portion(s) 314 of lever members 301a and 301b may be configured to receive one or more forces to translate or activate one or more ends 303a and 303b in contacting portions 322 to apply pressure to, or release pressure from, an anatomical object 309 or the like. In at least one example, applied force regions 314 of lever members 301a and 301b may include protrusions 381 or any other surface treatment (including dimples, cavities, holes, ridges, etc.) to facilitate an enhanced grip by a surgeon's hand (or any other person's hand). Protrusions 381 may enhance frictional forces to reduce slippage, and may provide a structure for receiving a lift force, which may increase a grip when surgical forceps 301 are lifted. Further, applied force portions 314 in some examples may be disposed on one side of a bisecting plane 344, the one side being proximal to pivot axes 302a and 302b. In this example, bisecting plane 344 is disposed at a bisecting distance 313 relative to a pivot axis or proximal end (e.g., at rotation axis 304) of surgical instrument 301. Hence, bisecting plane 344 may be disposed at or adjacent one-half of length 312 of surgical instrument 301. In various examples, an applied force may be imparted upon one or more of applied force portions 314 by a human operator (e.g., under manually-operation) or, in some cases, by a robotic-controlled force generation mechanism (e.g., via a linear motor). In some examples, one or more ends 303a and 303b of contacting portion 322 may be implemented as jaws of a pair of forceps.

Effective portion 316 may be a portion of either lever members 301a and 301b, or both, that facilitates implementation of surgical instrument 301 to access various depths at which to engage object 309. In some examples, effective region 316 provides a portion of length 312 to facilitate access to an internal surgical site as well as to navigate around and about obstacles during surgery (e.g., other surgeons' hands, other tools, such as clamps, internal anatomy, and any other encumbrance). Further, effective portions 316, may, in some examples, be disposed on one side of a bisecting plane 344, the one side being distal to pivot axes 302a and 302b, and adjacent to contacting portions 322 of lever members 301a and 301b. Note that contacting portions 322, including distal ends 303a and 30b, may be formed as part of effective portion 316, and may have any shape, such as straight, curved, or angled. Further, contacting portions 322 may include smooth or textured surfaces (e.g., cross-hatched), as well as a serrations or teeth. Contacting portions 322 also may include rings, cups, grooves, or any other engagement shape adapted to a particular purpose. For example, contacting surfaces at ends 303a and 303b may be configured to grip, clamp, grasp, join, support, compress or hold object 309, which may include bodily structures such as tissues, organs, arteries, vessels, veins, bones, etc. Object 309 may also include sponges, swabs, gauze or medical instruments, such as suture needles or other surgical items.

As shown, coupling member 390 may be configured to position pivot axes 302a and 302b at a distance 305 from each other. In some examples, distance 305 is along a line perpendicular to a longitudinal plane 340. In various examples, coupling member 390 may be configured to include any structure that provides for a displacement arm 306 extending from longitudinal plane 304 to pivot axis 302b, and another displacement arm 306 extending from longitudinal plane 304 to pivot axis 302a at a distance 305 from each other. In one closed state (or closing state) distal ends 303a and 303b may directly contact each other, or may contact an object 309 with which to engage. In various examples, distance 305 between pivot axes 302a and 302b may be greater than a distance between distal ends 303a and 303b.

In some examples, lever member 301a and a lever member 301b may have physical configurations and dimensions that may be described as a function of a longitudinal axis (e.g., a lever longitudinal axis) passing length-wise through a lever member. In some examples, a longitudinal axis of a lever member may be a line passing through each centroid of a number of cross sections of a lever member. A longitudinal axis need not reside internal to a lever member. In this example, a physical orientation or configuration of lever member 301a, as well as its functionality, may be described relative to a lever longitudinal axis 384, whereas a physical orientation or configuration of lever member 301b may be described relative to a lever longitudinal axis 385. Further, lever members 301a and 301b and any of their constituent elements may be configured to have any length and width dimension. Therefore, an applied force portion 314, such as an applied force of lever members 301a and 301b, and effective portions 316 may be configured to have any length dimension. While diagram 300 depicts lever members 301a and 301b having a substantially straight shape, lever members 301a and 301b may be formed to include or have any shape, such as curves, bends, etc.

In some examples, consider surgical instrument 301 may have a length 312 of 12 inches from, for example, rotation axis 304 to distal ends 303a and 303b. Exemplary forces applied at or about bisecting plane 344 may range from approximately 4 Newtons to approximately 32 Newtons may generate a range of pressures at distal ends 303a and 303b (e.g., from approximately 1.6 MPa to approximately 1.74 MPa of pressure). Bisecting plane 344 may be disposed at bisecting distance 394, which may be about 50% of length 312 (e.g., about 6 inches). In this case, surgical instrument 301 and its configuration may be provide efficiencies from at or about 7 to 16 times more pressure at distal ends 303a and 303b than otherwise might be the case.

By contrast, forces applied at or about $\frac{2}{3}^{rd}$ distance 392 from distal ends 303a and 303b may range from approximately 4 Newtons to approximately 2.7 Newtons to generate another range of pressures at distal ends 303a and 303b (e.g., from approximately 0.80 MPa to approximately 2.7 MPa of pressure). $\frac{2}{3}_{rd}$ distance 392 may be about 66.70% of length 312 (e.g., about 8 inches). In this case, surgical instrument 301 and its configuration may be provide efficiencies from at or about 4 to 13 times more pressure at distal ends 303a and 303b than otherwise might be the case. In some examples, amounts of pressures at distal ends 303a and 303b may be determined using, for instance, Fujifilm® FPD-8010E digital pressure mapping system, which is developed and maintained by Fujifilm of Tokyo, Japan.

In view of the foregoing, a surgeon implementing surgical instrument 301 (or any other instrument configuration described hereinafter) may be able to apply relatively less force to grasp and hold tissue. Efficiencies described above may facilitate reduced fatigue that a surgeon may experience when grasping and holding tissue in the operating room for extended periods of time. Note further that the amounts of forces applied (e.g., Newtons) and resulting amounts of pressures (e.g., MPa) are recited as example amounts and are not intended to be limiting. Thus, any amount of forces may be applied to generate any amount of pressures at distal ends 303a and 303b.

Figure 4:
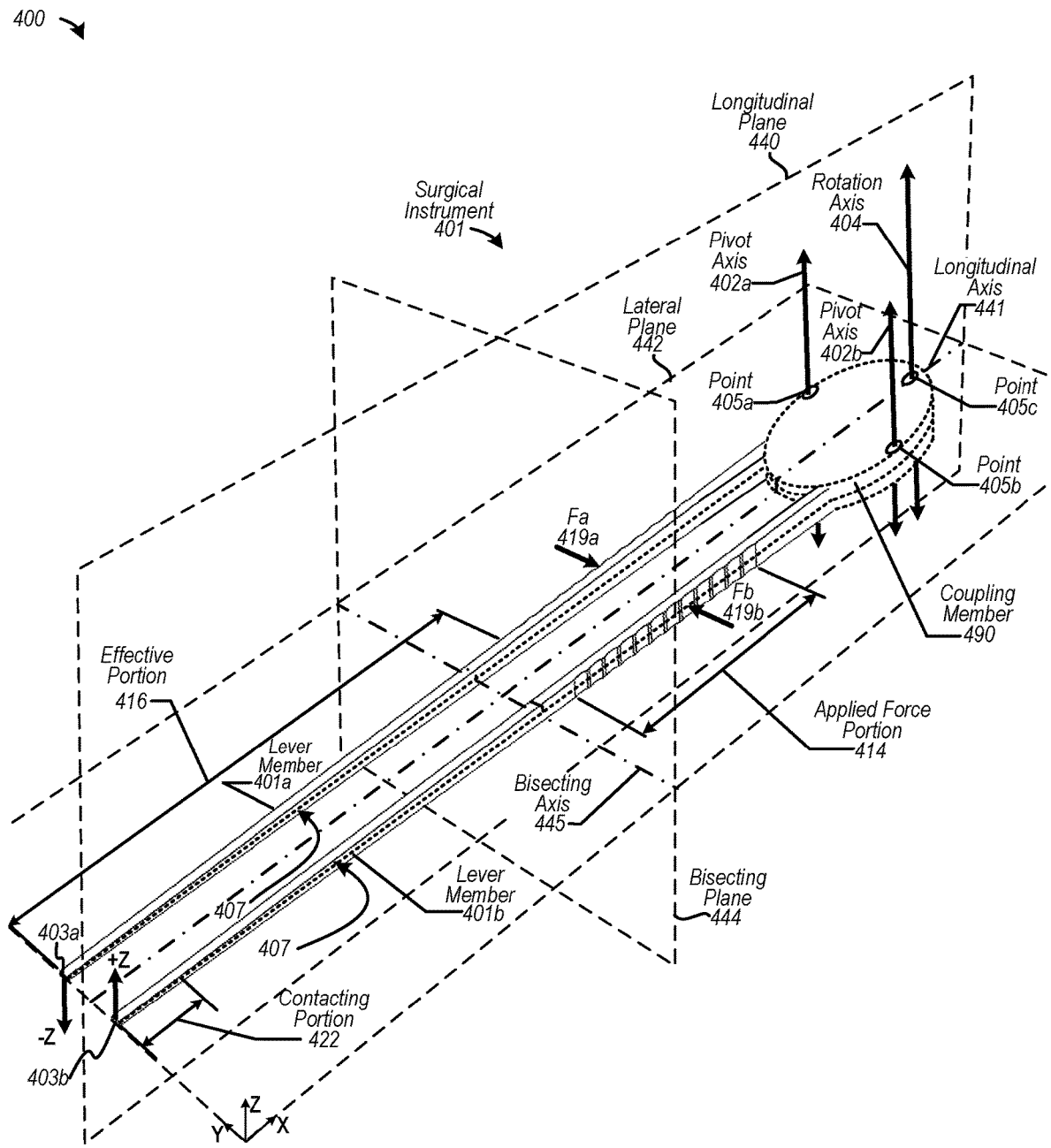
FIG. 4 is a diagram depicting a perspective view of an example of a surgical instrument implementing a coupling member including multiple pivot axes, according to some embodiments.

FIG. 4 is a diagram depicting a perspective view of an example of a surgical instrument implementing a coupling member including multiple pivot axes, according to some embodiments. Diagram 400 depicts a surgical instrument 401 including a lever member 401a and a lever member 401b each coupled to a coupling member 490, which is a distributive coupling member that distributes or positions multiple pivot axes 401a and 401b at a distance from each other (e.g., a distance perpendicular to the longitudinal axis 441). Each lever member 401a and lever member 401b include an applied force portion 414, an effective portion 416, and a contacting portion 422, which includes ends 403a and 403b.

Diagram 400 also shows a surgical instrument 401 and its constituent elements depicted relative to a longitudinal plane 440, a longitudinal plane 442, and a bisecting plane 444, in at least one example. Longitudinal plane 440 may intersect lateral plane 442 at a longitudinal axis 441, and substantially divides surgical instrument 401 into two halves, whereby one half includes lever member 401a and the other half includes lever member 401b. Lateral plane 442 is orthogonal to longitudinal plane 440 and substantially divides each of surgical instrument 401 and lever members 401a and 401b into symmetrical halves along, for example, plane-intersection lines 407. As shown, lateral plane 442 may include point 405a and point 405b at which a pivot axis 402a and a pivot axis 402b, respectively, intersect lateral plane 442. Further, lateral plane 442 may include a point 405c at which a rotation axis 404a intersects lateral plane 442. In operation, lever members 401a and 401b rotate about pivot axis 402a and pivot axis 402b, respectively, in lateral plane 442. Bisecting plane 444 divides a length of surgical instrument 401 along longitudinal axis 441 in half, and may intercept lateral plane 442 at a bisecting axis 445.

In operation, consider an example in which applied forces ("Fa") 419a and ("Fb") 419b are directed to associated applied force portions 414. Responsive to receiving applied forces 419a and 419b, ends 403a and 403b may traverse within lateral plane 442 toward each other. For example, ends 403a and 403b may rotate within lateral plane 442 relative to pivot axes 402a and 402b, respectively. In some examples, surgical instrument 401 and any of its constituent elements, such as, coupling member 490 and lever members 401a and 401b, as well as corresponding applied force portions 414, effective portions 416, and contacting portions 422 each may be dimensioned to stabilize ends 403a and 403b during operation (e.g., prevent scissoring or displacement of end 403a in a −Z direction and 403b in a +Z direction that may cause lever members to cross over each other). For example, a dimension parallel to an X-Z plane for coupling member 490 may be sized to enhance stabilization of ends 403a and 403b. In addition, surgical instrument 401 and any of its constituent elements may be dimensioned to, for example, reduce a resistance of a material to elastically deform (e.g., reduce elastic modulus of a material, such as metal). For example, a dimension (e.g., a thickness) parallel to an Y-Z plane of coupling member 490 or lever member 401a and a lever member 401b may be sized to provide for enhanced flexion (e.g., at a pivot axis, a pivoting region, and/or at a flexion region).

Figure 5A:
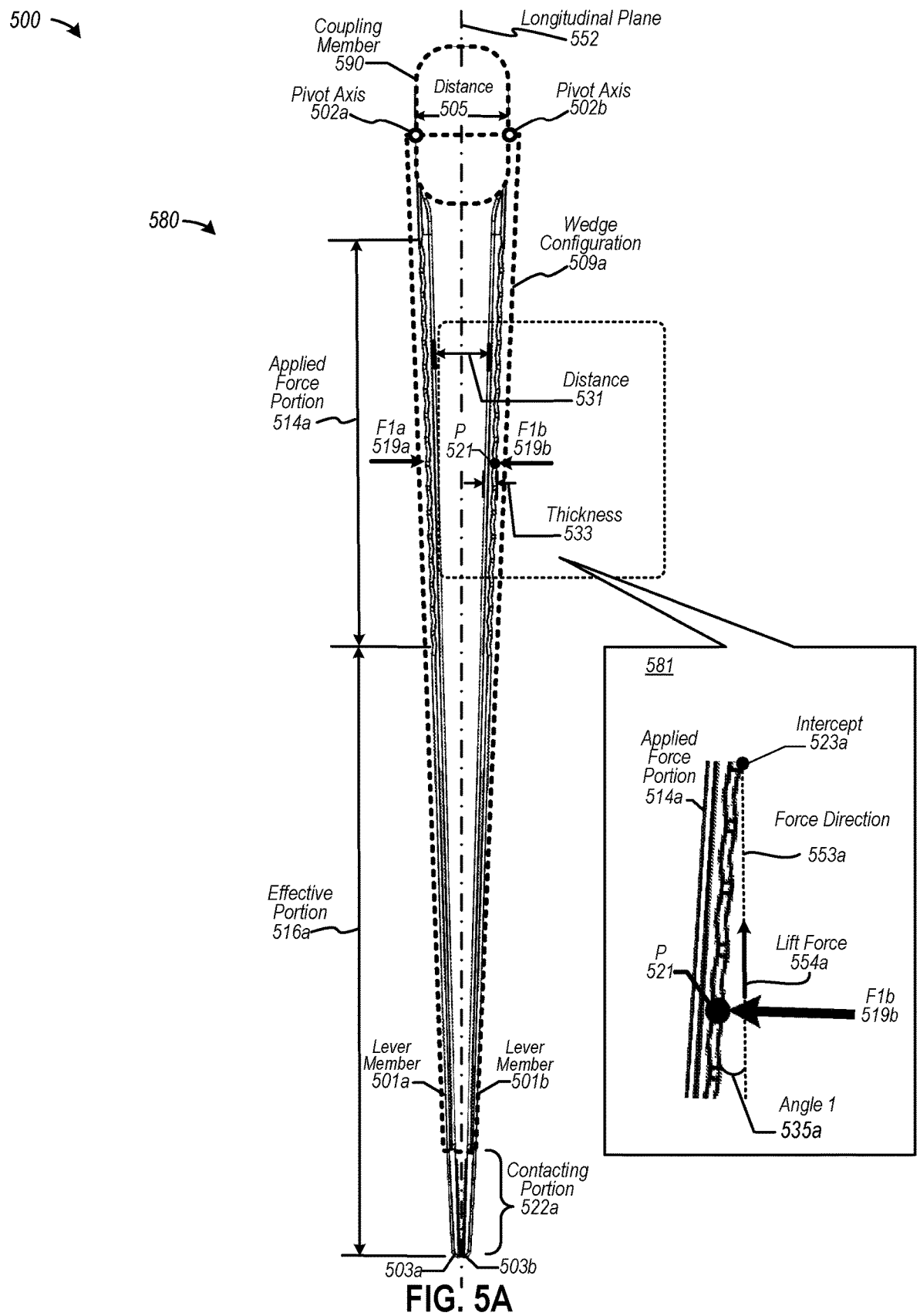
FIGS. 5A and 5B are diagrams depicting a surgical instrument in various examples of closing states, according to some embodiments.
Figure 5B:
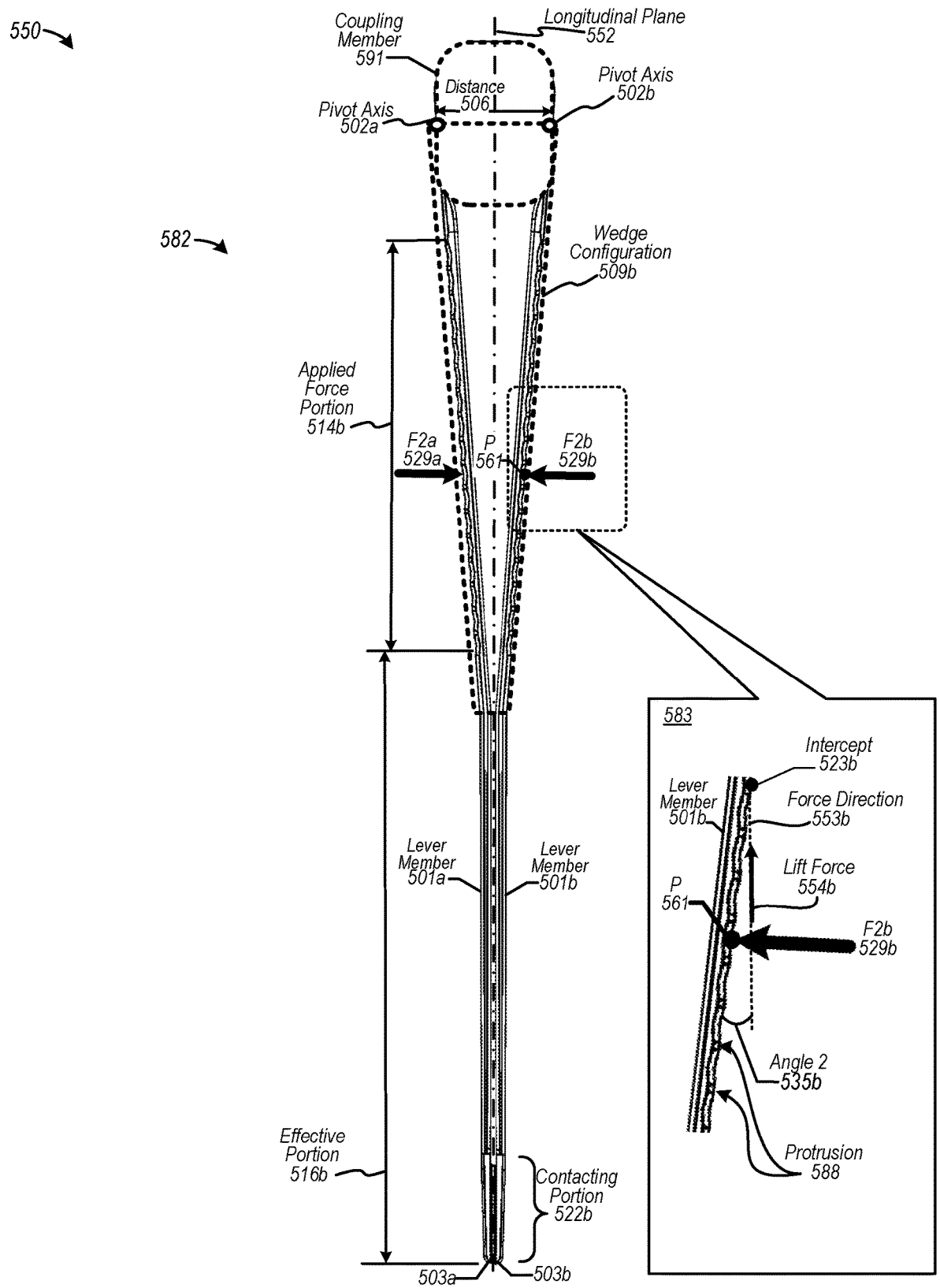

FIGS. 5A and 5B are diagrams depicting a surgical instrument in various examples of closing states, according to some embodiments. Diagram 500 of FIG. 5A depicts a surgical instrument 580 including a coupling member 590 coupled via pivot axis 502a and pivot axis 502b to a lever member 501a and a lever member 501b, respectively. Each of lever members 501a and 501b may include an applied force portion 514a, an effective portion 516a and a contacting portion 522a, which may include ends at 503a and 503b. As shown, coupling member 590 may be configured to position pivot axis 502a and pivot axis 502b at a distance 505 from each other (e.g., in a direction perpendicular to a longitudinal plane 552).

In the example shown, applied forces ("F1a") 519a and ("F1b") 519b are directed to associated applied force portions 514a. For example, force 519b may be directed to point ("P") 521 on or adjacent to one of applied force portions 514a. Applied forces 519a and 519b may be of sufficient magnitude to rotate lever members 501a and 501b such that ends 503a and 503b touch in a first closing state. In some cases, a portion of surfaces of contacting portions 522a may yet to touch or engage with each other. In this configuration, distance 505 is greater than the distance between ends 503a and 503b, and lever members 501a and 501b (and applied force portions 514a) form a wedge configuration 509a.

Further to the example shown, consider surgical instrument 580 may be used to lift an object in a direction, for example, parallel to longitudinal plane 552. As shown within inset 581, applied force 519b (or a portion thereof) is applied at point 521 in a direction, for example, orthogonal (or substantially orthogonal) to a surface of applied force portion 514a. Based on wedge configuration 509a, a second applied force may be applied to or adjacent point 521. At least a portion of second force portion may be a lift force 554a having a force direction 553a, which intercepts a surface portion of applied force portion 514a at intercept point 523a. In some examples, force direction 553a may be applied to a protrusion (not shown) that may be configured to direct a greater magnitude of force into surgical instrument 580. The force direction 553a may be at an angle ("1") 535a. Thus, at least a portion of lift force 554a is applied to (e.g., directly to) surgical instrument 580.

FIG. 5B is a diagram 550 depicting a surgical instrument 582 including a coupling member 591 coupled via pivot axis 502a and pivot axis 502b to a lever member 501a and a lever member 501b, respectively. Each of lever members 501a and 501b may include an applied force portion 514b, an effective portion 516b and a contacting portion 522b, which may include ends at 503a and 503b. As shown, coupling member 591 may be configured to position pivot axis 502a and pivot axis 502*b* at a distance 506 from each other (e.g., in a direction perpendicular to a longitudinal plane 552).

In the example shown, applied forces ("F2a") 529*a* and ("F2b") 529*b* are directed to associated applied force portions 514*b*, whereby applied forces 529*a* and 529*b* may be greater in magnitude than applied forces 519*a* and 519*b* of FIG. 5A. A shown in this example, force 529*b* of FIG. 5B may be directed to point ("P") 561 on or adjacent to surface portions of one of applied force portions 514*b*. Applied forces 529*a* and 529*b* may be of sufficient magnitude to further rotate lever members 501*a* and 501*b* such that ends 503*a* and 503*b* touch in a second closing state. Also, portions of surfaces of contacting portions 522*a* may touch or engage with each other, and, optionally, portions of effective portion 516*b* may traverse closer to each (e.g., based on flexion of lever members 501*a* and 501*b*). In this configuration, distance 506 is greater than the distance between ends 503*a* and 503*b*, and lever members 501*a* and 501*b* (and applied force portions 514*b*) form a wedge configuration 509*b*.

Further to the example shown, consider surgical instrument 582 may be used to lift an object in a direction, for example, parallel to longitudinal plane 552. As shown within inset 583, applied force 529*b* (or a portion thereof) may be applied at point 561 in a direction, for example, orthogonal (or substantially orthogonal) to a surface of applied force portion 514*b*. Based on wedge configuration 509*b*, a second applied force may be applied to or adjacent point 561. At least a portion of second force portion may be a lift force 554*b* having a force direction 553*b*, which intercepts a surface portion of applied force portion 514*b* at intercept point 523*b*. In some examples, force direction 553*b* may be applied to a protrusion 588 that may be configured to direct a greater magnitude of force into surgical instrument 582. The force direction 553*b* may be at an angle ("2") 535*b*, which may be a greater angle than angle ("1") of FIG. 5A. As such, a greater angle 535*b* between force direction 553*b* and lever member 501*b* facilitates a greater magnitude of force directed into surgical instrument 582 to facilitate lifting an object, for example.

In view of the foregoing and descriptions herein, surgical instrument 582 may be configured to establish, for example, distance 506, which, in turn, provides for a relatively increased amount of distance for which to place a pad of a thumb and a pad on an index finger, as an example. In at least one embodiment, coupling member 591 provides for an amount of distance that enhances, for example, a "pinch distance" in association with application of 529*a* and 529*b* on surgical instrument 582. Also, in at least some examples, a distance 531 of FIG. 5A between lever member 501*a* and lever member 501*b* (and a thicknesses 533 thereof) may be facilitated based on distance 506. In some implementations, a distance 531 (e.g., a pinch distance) may provide a range of movement to provide an enhanced force at ends 503*a* and 503*b* as a function, for example, distance 506. According to some examples, distance 531 enables a user (e.g., a surgeon) a greater range of motion with which to apply various graduated increments of force via ends 503*a* and 503*b* than otherwise might be the case.

Figure 6:
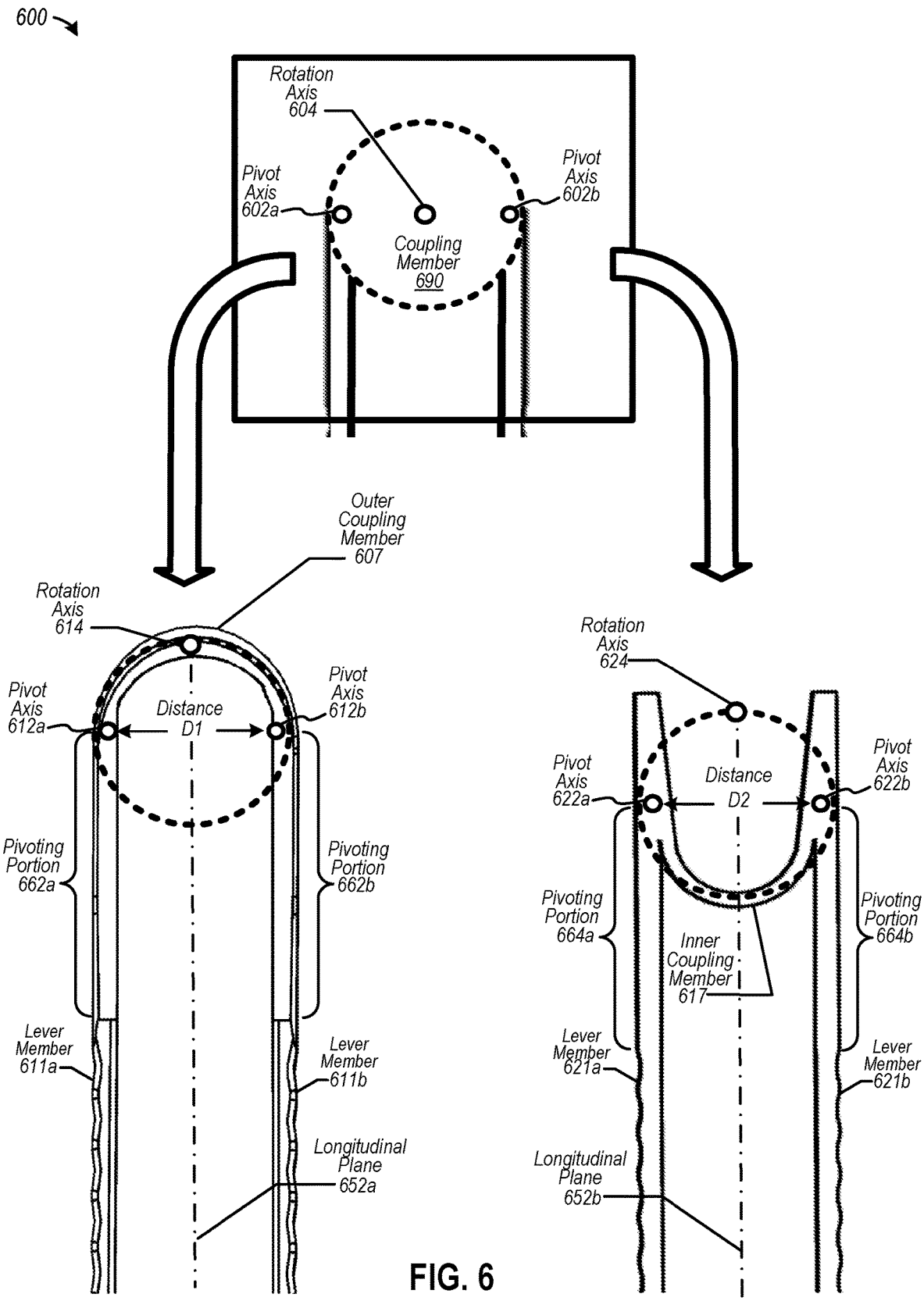
FIG. 6 is a diagram depicting examples of a coupling member, according to some embodiments.

FIG. 6 is a diagram depicting examples of a coupling member, according to some embodiments. Diagram 600 depicts a coupling member 690 including a rotation axis 604 and pivot axes 602*a* and 602*b*. As shown, coupling member 690 may be formed as an outer coupling member 607 or as an inner coupling member 617. Outer coupling member 607 may be configured to include or couple to a lever member 611*a* and a lever member 611*b* at or adjacent to a pivot axis 612*a* and a pivot axis 612*b*, respectively. In some examples, pivot axis 612*a* and pivot axis 612*b* may be configured to facilitate rotation of lever member 611*a* relative to pivot axis 612*a* and rotation of lever member 611*b* relative to pivot axis 612*b*. In some examples, pivot axis 612*a* and pivot axis 612*b* may be implemented as a pivoting portion 662*a* and a pivoting portion 662*b*, respectively, whereby pivoting portions 662*a* and 662*b* may be formed or implemented as portions of a corresponding lever member. Any of pivoting portions 662*a* and 662*b* may be configured to facilitate rotation of distal ends (not shown) of lever members 611*a* and 611*b* about, for example, a rotation axis 614 to effect a closing state. For example, any of pivoting portions 662*a* and 662*b* may be formed to include a material or may be constructed to reduce a resistance of a material to elastically deform (e.g., reduce elastic modulus of a material, such as metal), thereby enabling material at pivoting portions 662*a* and 662*b* to bend responsive to forces applied to lever members 611*a* and 611*b*. As shown, rotation axis 614 may lie in a longitudinal plane 652*a* at a proximal end of a surgical instrument, thereby using a length of that surgical instrument, according to at least some examples.

Further, diagram 600 depicts inner coupling member 617 including a rotation axis 624 and pivot axes 622*a* and 622*b* at which a lever member 621*a* and a lever member 621*b* may be coupled respectively. In some examples, pivot axis 622*a* and pivot axis 622*b* may be configured to facilitate rotation of lever member 621*a* relative to pivot axis 622*a* and rotation of lever member 621*b* relative to pivot axis 622*b*. In some examples, pivot axis 622*a* and pivot axis 622*b* may be implemented as a pivoting portion 664*a* and a pivoting portion 664*b*, respectively, whereby pivoting portions 642*a* and 642*b* may be formed or implemented as portions of a corresponding lever member. Any of pivoting portions 664*a* and 664*b* may be formed to include a material property to facilitate bending responsive to forces applied to lever members 621*a* and 621*b*. As shown, rotation axis 624 may lie in a longitudinal plane 652*b* adjacent a proximal end of a surgical instrument and need not reside in or on material forming the surgical instrument. In some cases, distance D2 between pivot axes 622*a* and 622*b* facilitates disposition of rotation axis 624 relative to rotation of distal ends (not shown) of lever members 621*a* and 621*b*.

Figure 7A:
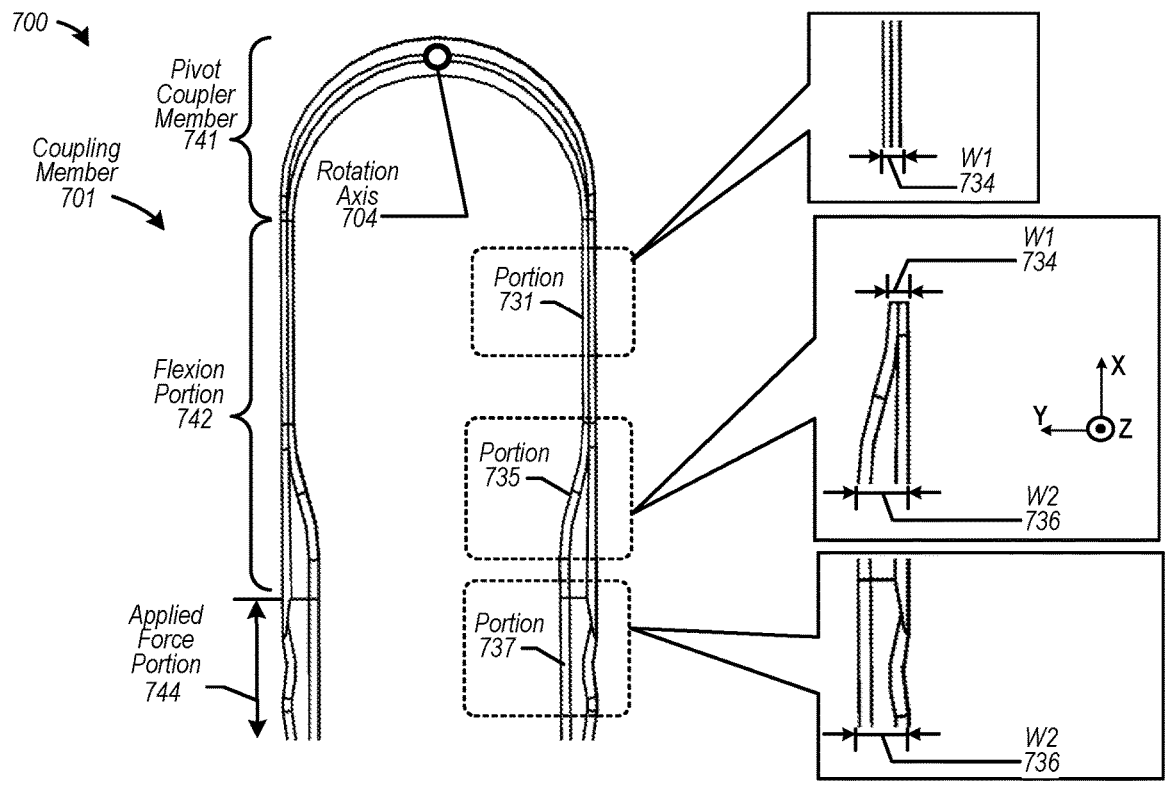
FIGS. 7A to 7C are diagrams depicting various examples of flexion portions implemented as pivoting portions in accordance with various embodiments.
Figure 7B:
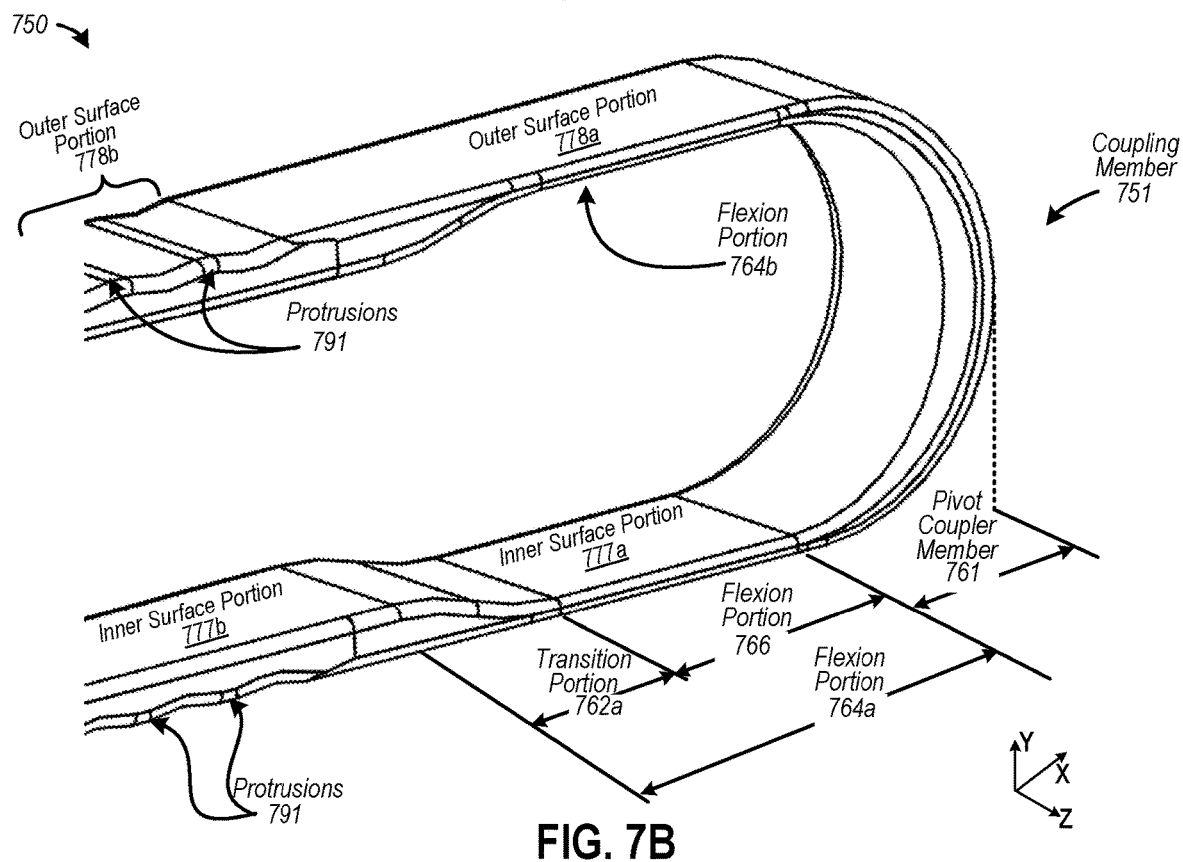
Figure 7C:
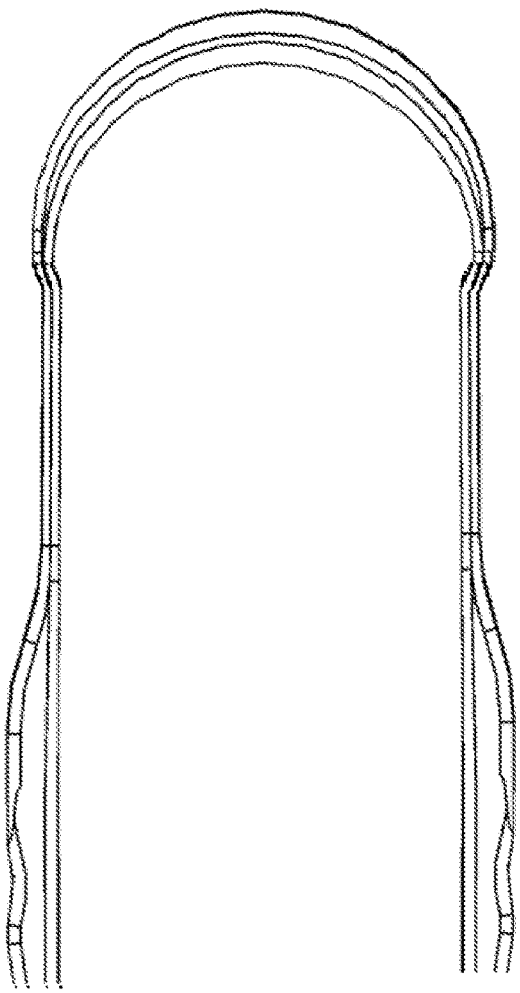

FIGS. 7A to 7C are diagrams depicting various examples of flexion portions implemented as pivoting portions in accordance with various embodiments. Diagram 700 of FIG. 7A includes a coupling member 701 coupled to an applied force portion 744, according to some examples. Further, coupling member 701 may include pivot coupler member 741 and may optionally include a flexion portion 742, whereby flexion portion 742 may be implemented as a pivoting portion (or a pivot axis) to facilitate rotation of distal ends of a surgical instrument (not shown) relative to a rotation axis 704. In some examples, a portion 731 may be formed to have a dimensioned width ("W1") 734, which is less than a dimensioned width ("W2") 736 of applied force portion 744. Dimensioned width 734 may be configured or sized to promote flexion to rotate the distal ends responsive to amount of forces applied to applied force portions 744 of lever members. Further to diagram 700, flexion portion 742 may include a transition portion 735 at which dimensioned width 734 transitions to dimensioned width 736. In some instances, dimensioned widths 734 and 736 may be relative to (or in) a Y-Z plane. According to various examples, dimensioned widths 734 and 736 may be of any size. For example, dimensioned width 734 may be in a range from 30% to 40% of dimensioned width 736, or any other proportion, which may be a function of a type of material used (e.g., a type of metal used). In a non-limiting example, dimensioned widths 734 and 736 may be 1.0 mm and 4.0 mm, or any other amounts, in at least one implementation.

FIG. 7B is a diagram 750 depicting a perspective view of a coupling member including flexion portions, according to some examples. As shown, coupling member 751 may include pivot coupler member 761, a flexion portion 764*a*, and a flexion portion 764*b*, whereby diagram 750 depicts relative dimensions of flexion portions 764*a* and 764*b*. In some examples, flexion portion 764*a* may include a transition portion 762*a* and flexion portion 766. Further, dimensioned widths 734 and 736 of FIG. 7A may be relative to outer surfaces, which may provide a relatively constant reference. For example, outer surface portion 778*a* of flexion portion 764*b* and outer surface portion 778*b* of an applied force portion may be relatively constant (e.g., substantially in a same reference plane). Outer surface portion 778*b* of an applied force portion are shown to include protrusions 791. Thus, inner surface portion 777*b* and inner surface portion 777*a* of flexion portion vary relative in dimensions to each other. As such, flexion portions 764*a* and 764*b* are "inner" flexion portions.

FIG. 7C is a diagram 780 includes a coupling member 781 coupled to an applied force portion 786, according to some examples. As shown, coupling member 781 may include pivot coupler member 782, an external flexion portion 784, and an applied force portion 786, whereby diagram 750 depicts relative dimensions of external flexion portion 784 and applied force portion 786. In this example, inner surface portions of external flexion portion 784 and applied force portion 786 may be relatively constant (e.g., substantially in a same reference plane). Thus, outer surface portions of flexion portion 784 and applied force portion 786 vary relative in dimensions to each other. As such, external flexion portion 784 is an "outer" flexion portions. In some examples, a thinner portion (e.g., flexion portion) disposed on an outer surface, such as external flexion portion 784, may be configured to enhance an amount of leverage (e.g., an additional 2 mm of leverage) to generate ranges of pressures at the distal ends.

Figure 8A:
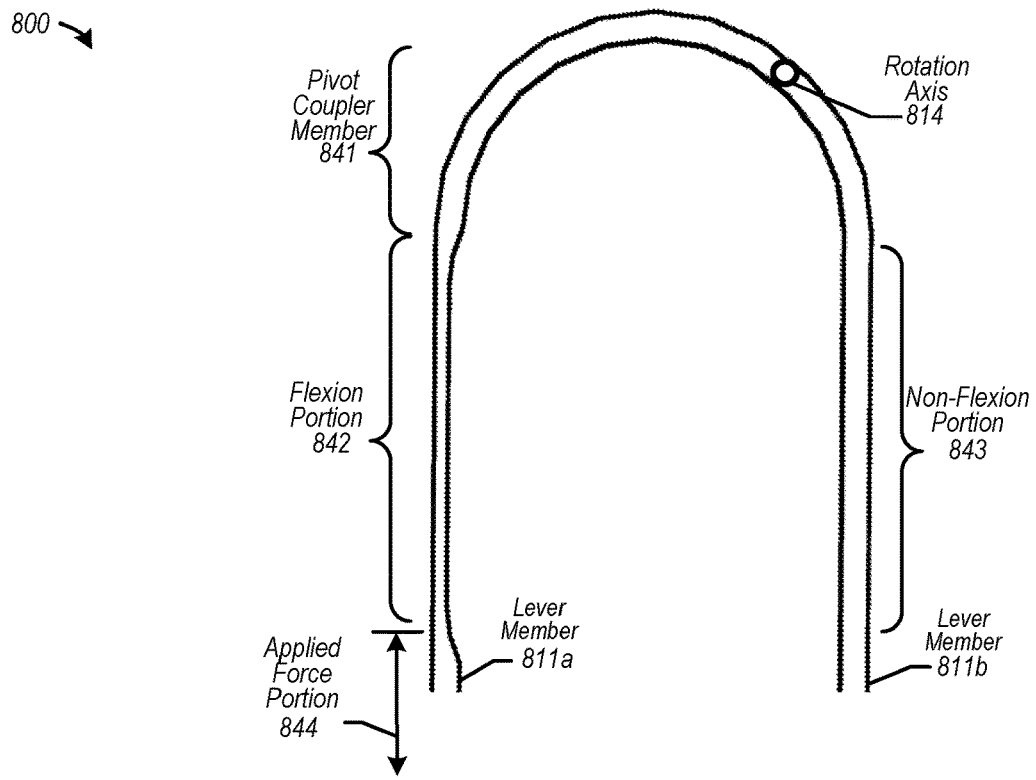
FIGS. 8A to 8B are diagrams depicting various other examples of flexion portions implemented as pivoting portions in accordance with some embodiments.
Figure 8B:
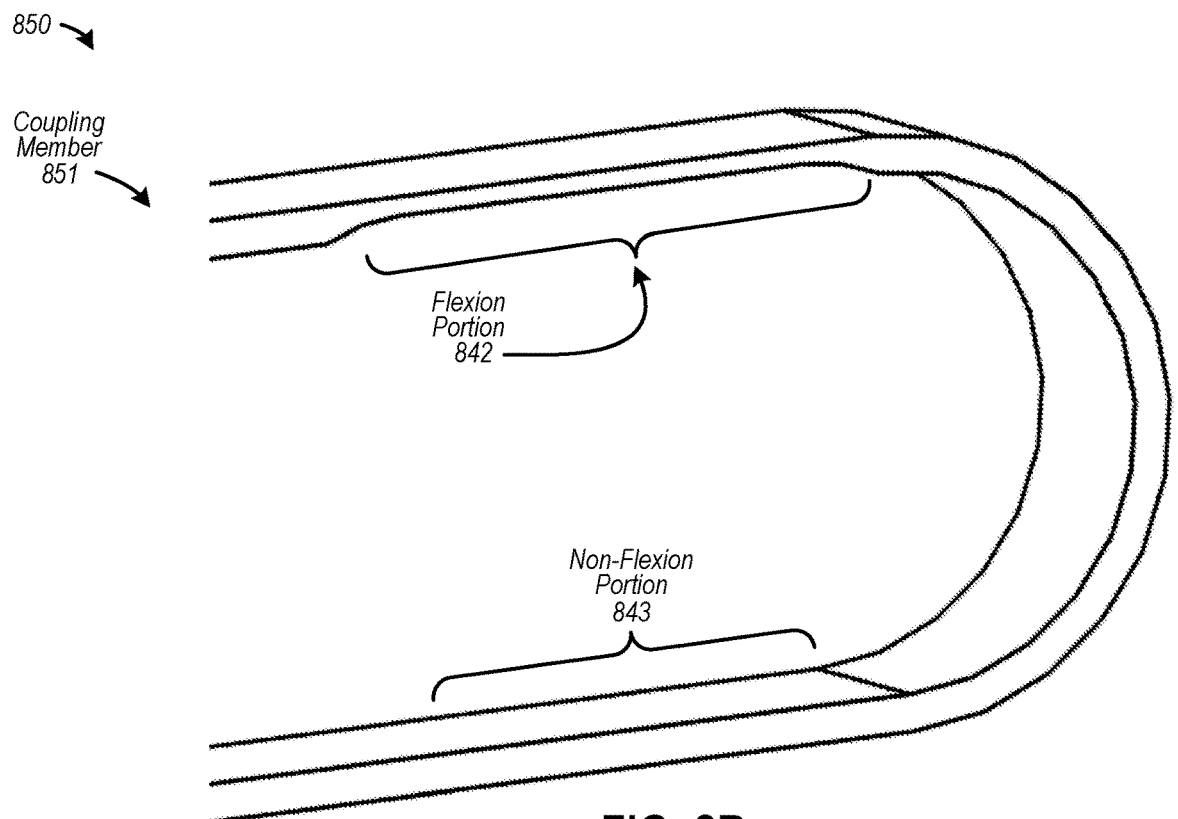

FIGS. 8A to 8B are diagrams depicting various other examples of flexion portions implemented as pivoting portions in accordance with various embodiments. Diagram 800 of FIG. 8A includes a coupling member coupled to a lever member 811*a*, the coupling member including a pivot coupler member 841 and a flexion portion 842. Lever member 811*a* is shown to also include an applied force portion 844. By contrast, lever member 811*b* omits a flexion portion at a region depicted as a non-flexion portion 843. Therefore, lever member 811*b* may remain relatively stationary as an applied force impinges on applied force portion 844 to rotate an end (not shown) associated with lever member 811*a*. In some examples, non-flexion portion 843 may shift or alter a rotation axis 814 adjacent closer to lever member 811*b*, as shown.

FIG. 8B is a diagram 850 depicting a perspective view of a coupling member including a non-flexion portion, according to some examples. As shown, coupling member 851 may include a flexion portion 842 and a non-flexion portion 843.

Figures 9A, 9B:
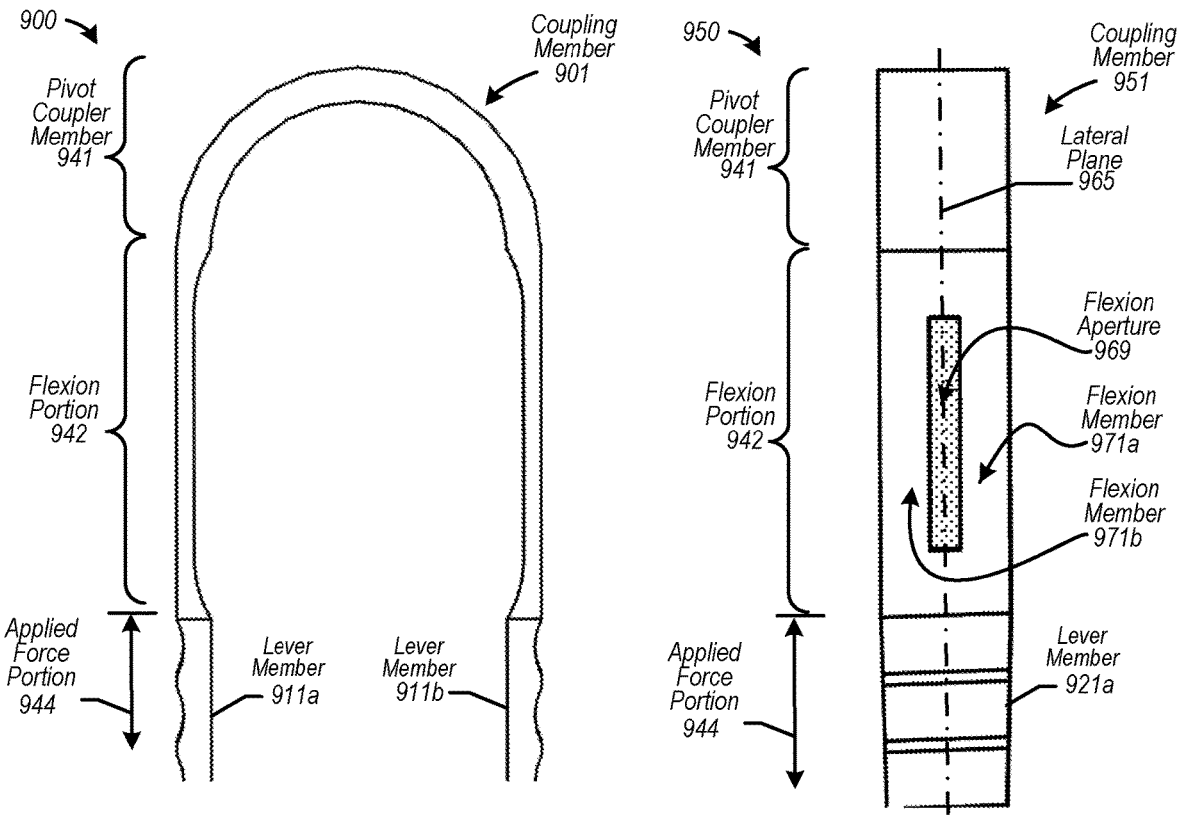
FIGS. 9A to 9C are diagrams depicting various alternative examples of flexion portions implemented as pivoting portions in accordance with some embodiments.
Figure 9C:
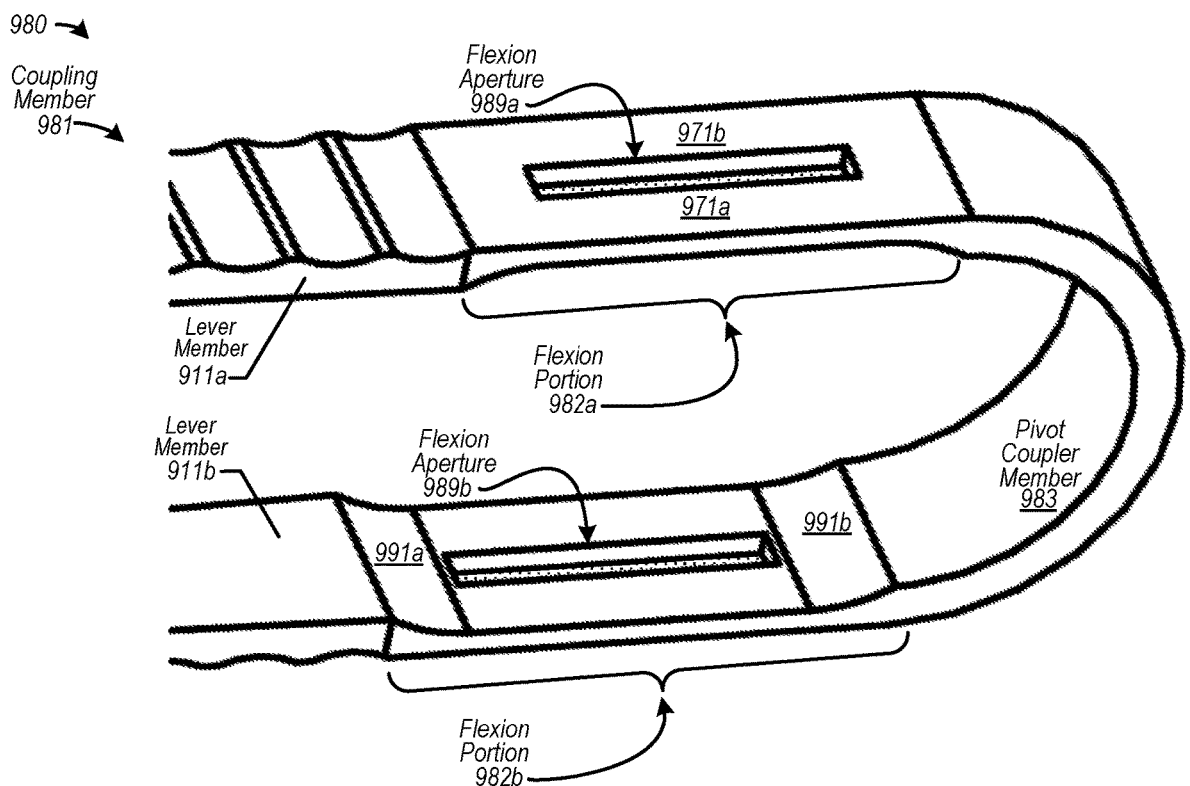

FIGS. 9A to 9C are diagrams depicting various alternative examples of flexion portions implemented as pivoting portions in accordance with various embodiments. Diagram 900 of FIG. 9A includes a coupling member 901 coupled to a lever member 911*a*, and coupling member 901 includes a pivot coupler member 941 and a flexion portion 942. Lever member 911*a* is shown to also include an applied force portion 944. As shown, lever member 911*b* may also include flexion portion 942.

FIG. 9B is a diagram 950 depicting a side view of a coupling member 951 coupled to a lever member 921*a*, and coupling member 951 includes pivot coupler member 941 and flexion portion 942. Lever member 921*a* is shown to also include applied force portion 944. Further, flexion portion 942 may be configured to include a flexion aperture 969 to modify a material property of flexion portion 942 (e.g., modify a resistance of a material to elastically deform to promote enhance ability to bend with reduced application of force). In some examples, flexion portion 942 may include a flexion member 971*a* and a flexion member 971*b* that are configured to couple coupling member 951 to applied force portion 944. Flexion member 971*a* and flexion member 971*b* may be dimensioned to form a flexion aperture 969 (e.g., along a portion of a lateral plane 965 or another plane parallel thereto), whereby dimensions of flexion aperture 969 may influence determining a degree of flexibility of flexion portion 942. Hence, absence of a material at flexion aperture 969 may enhance flexibility of flexion portion 942.

FIG. 9C is a diagram 980 depicting a perspective view of a coupling member 981 and flexion portions 982*a* and 982*b* having flexion apertures 989*a* and 989*b*, respectively, according to some examples. As shown, a coupling member 981 may include a pivot coupler member 983 coupled via flexion portion 982*a* to a lever member 911*a*. Also, pivot coupler member 983 may further be coupled via flexion portion 982*b* to a lever member 911*b*. Flexion member 971*a* and flexion member 971*b* may be dimensioned to form a flexion aperture, such as flexion aperture 969. Diagram 980 also depicts transition regions 991*a* and 991*b* of flexion portion 982*b*.

Figure 10A:
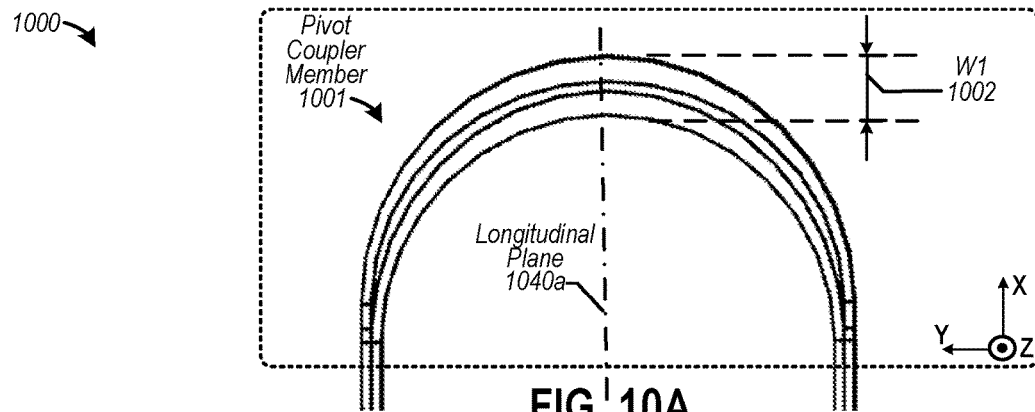
FIGS. 10A to 10C are diagrams depicting examples of a pivot coupler member configured to stabilize distal ends of a surgical instrument, according to some embodiments.
Figure 10B:
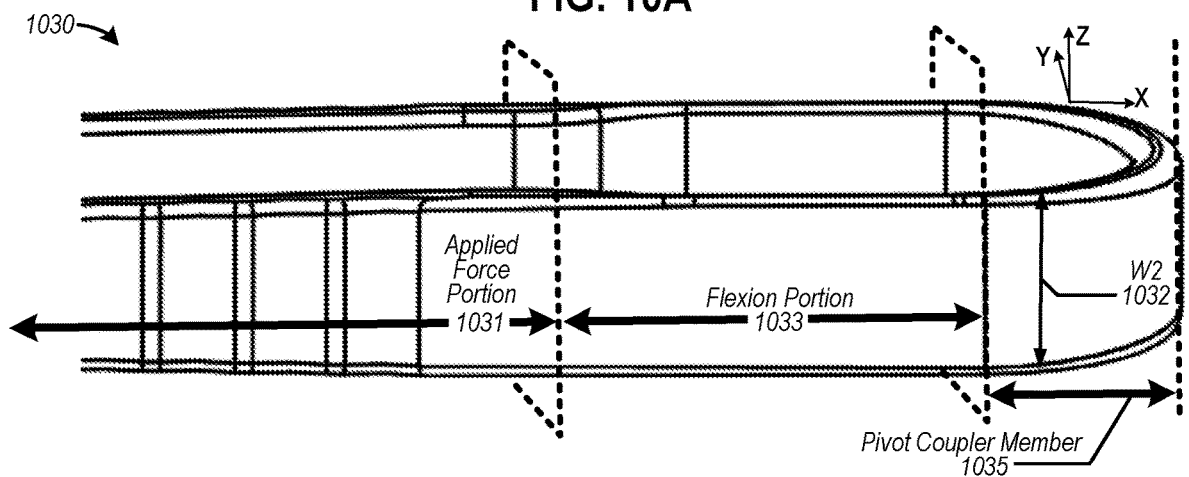
Figure 10C:
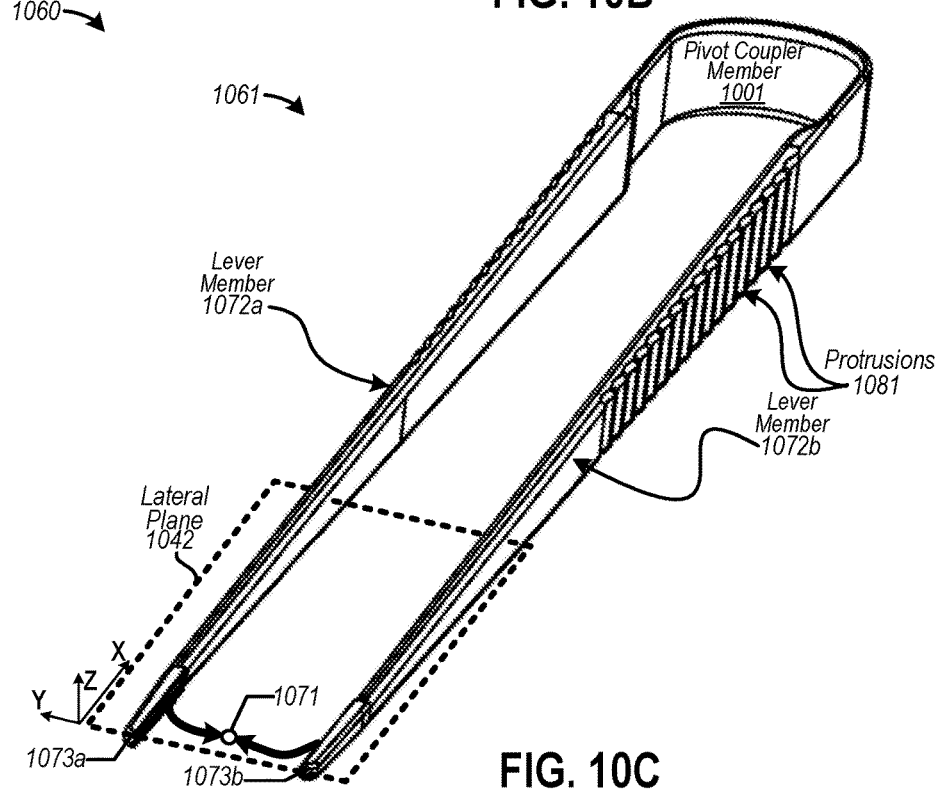

FIGS. 10A to 10C are diagrams depicting examples of a pivot coupler member configured to stabilize distal ends of a surgical instrument, according to some embodiments. FIG. 10A is a diagram 1000 depicting a pivot coupler member 1001 having a first dimensioned width ("W1") 1002. FIG. 10B is a diagram 1030 depicting a pivot coupler member 1035 having a second dimensioned width ("W2") 1032. Pivot coupler member 1035 may be coupled via a flexion portion 1033 to applied force portion 1031. FIG. 10C is a diagram 1060 depicting a perspective view of a surgical instrument 1061 including a pivot coupler member 1001 coupled to lever members 1072*a* and 1072*b*, which may include protrusions 1081. Pivot coupler member 1001 may be configured to stabilize and urge ends 1073*a* and 1073*b* to rotate in lateral plane 1042 to engage an object 1071. Therefore, pivot coupler member 1001 may be formed to reduce or prevent ends 1073*a* and 1073*b* from "scissoring" or "overlapping" each other (e.g., pivot coupler member 1001 may negate or decrease translation of ends 1073*a* and 1073*b* in a Z direction). In some non-limiting examples, dimensioned width ("W1") 1002 of FIG. 10A may be in a range from 20% to 30% of dimensioned width ("W2") 1032, or any other proportion, which may be a function of a type of material used (e.g., a type of metal used). In another non-limiting example, dimensioned widths 734 and 736 of FIG. 7A may be between, for example, 1.5 mm and 3.0, or any other amounts, in at least one implementation. In some examples, dimensioned widths 734 and 736 may be, for instances, at a 1 to 2 ratio (or any variation thereof).

Figure 11:
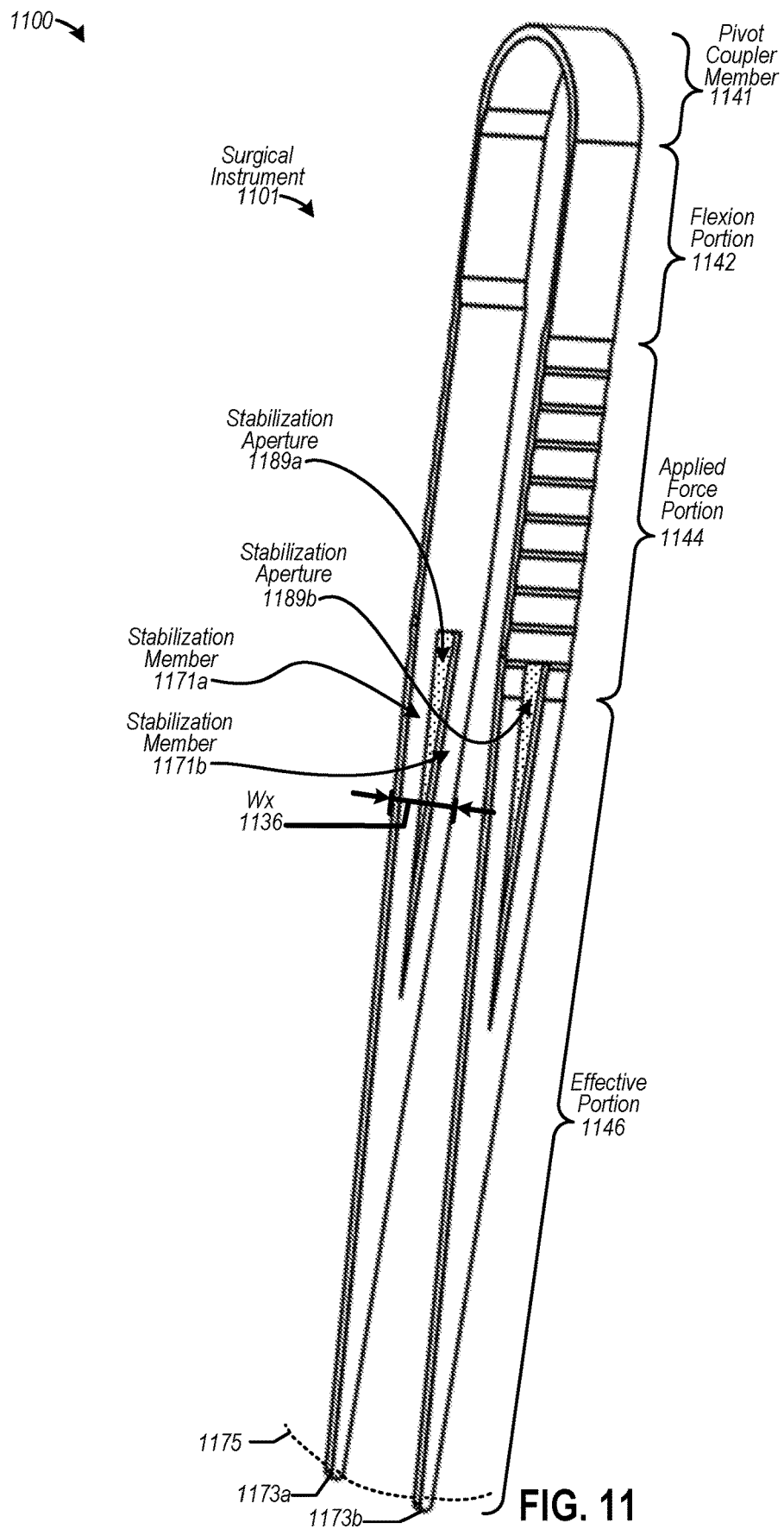
FIG. 11 is a diagram depicting an example of a surgical instrument implementing stabilization members in accordance with various embodiments.

FIG. 11 is a diagram depicting an example of a surgical instrument implementing stabilization members in accordance with various embodiments. Diagram 1100 depicts a surgical instrument 1101 including a pivot coupler member 1141 and lever members that include flexion portions 1142, applied force portions 1144, effective portions 1146, and ends 1173a and 1173b, which are configured to rotate in an arc 1175 in a lateral plane. As shown, surgical instrument 1101 may be configured to implement a stabilization member 1171a and a stabilization member 1171b in either an effective portion 1144 or applied force portion 1144, or both. Stabilization members 1171a and 1171b are configured to form a stabilization aperture 1189a of a first lever member (or stabilization aperture 1189b of a second lever member). According to various examples, an absence of material associated with stabilization aperture 1189a reduces a mass or weight of surgical instrument 1101. In turn, the material omitted from stabilization aperture 1189a may be used to increase a dimension ("Wx") 1136 along, for example, effective portion 1146 adjacent to ends 1173a and 1173b. Increased amount of dimension 1136 may promote or enhance stabilization of ends 1173a and 1173b to, for example, negate or reduce "scissoring" or "overlapping" ends 1073a and 1073b (e.g., ends 1073a and 1073b translate in a plane (or substantially in plane) that includes a range of motion or arc 1175). For example, ends 1073a and 1073b may be configured to translate in plane 1042 of FIG. 10C.

Figure 12:
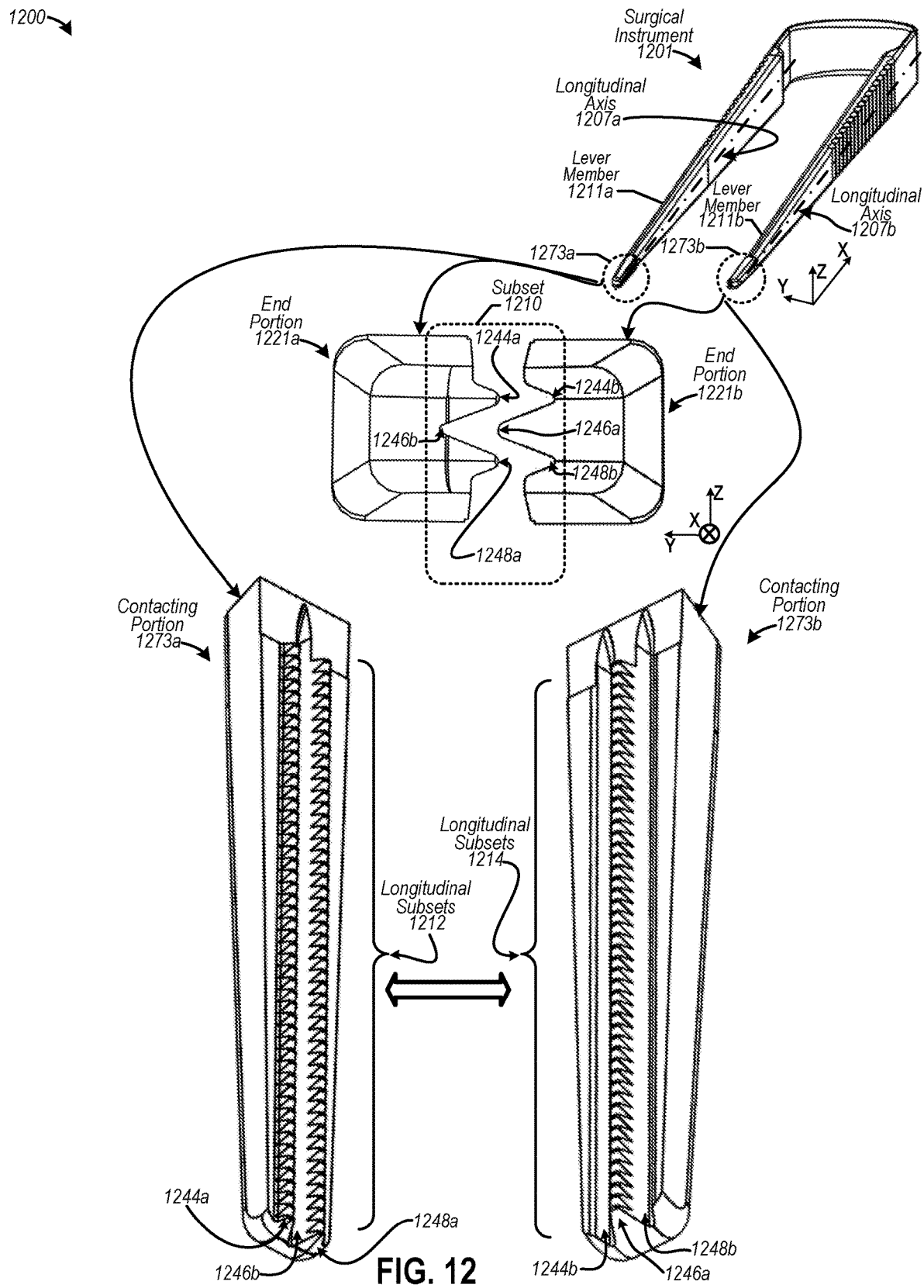
FIG. 12 is a diagram depicting an example of contacting portions of a surgical instrument in accordance with some examples.

FIG. 12 is a diagram depicting an example of contacting portions of a surgical instrument in accordance with some examples. Diagram 1200 depicts a surgical instrument 1201 including lever members 1211a and 1211b. Lever member 1211a may include a lever longitudinal axis 1207a and a contacting portion 1273a, whereas lever member 1211b may include a lever longitudinal axis 1207b and a contacting portion 1273b. Contacting portion 1273a includes an end portion 1221a having engagement teeth 1244a and 1248a, and a channel 1246b, whereas contacting portion 1273b includes an end portion 1221b having channels 1244b and 1248b and engagement tooth 1246a. In this example, a subset 1210 of engagement portions include engagement teeth 1244a, 1246a, and 1248a configured to engage or contact channels 1244b, 1246b, and 1248b. Further, diagram 1200 depicts subset 1210 as one subset of engagement portions in longitudinal subsets 1212 of contacting portion 1273a and longitudinal subsets 1214 of contacting portion 1273b.

Figure 13:
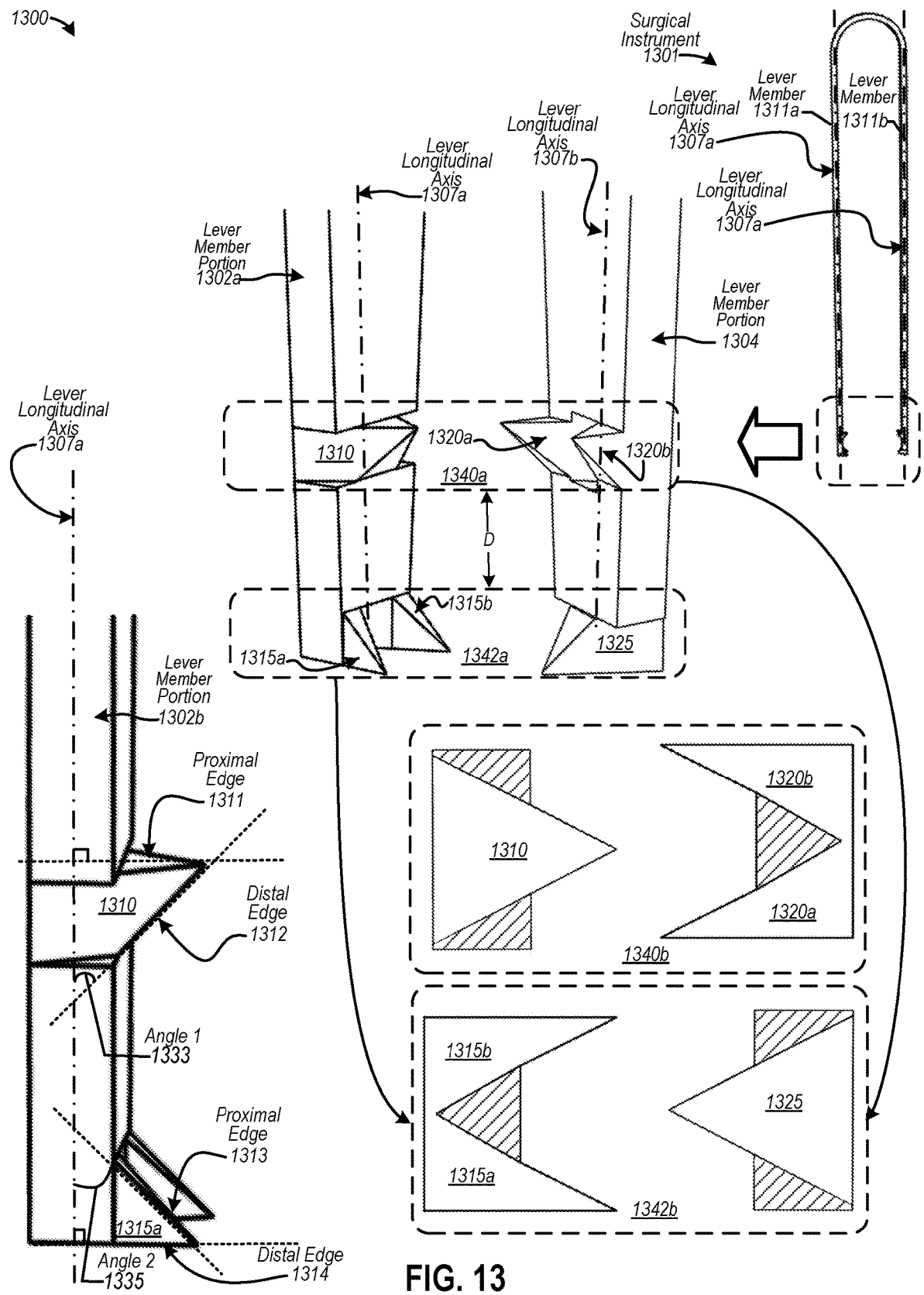
FIG. 13 is a diagram depicting another example of contacting portions of a surgical instrument, according to some examples.

FIG. 13 is a diagram depicting another example of contacting portions of a surgical instrument, according to some examples. Diagram 1300 depicts a surgical instrument 1301 including lever members 1311a and 1311b. Lever member 1311a may include a lever longitudinal axis 1307a and a lever member portion 1302a, whereas lever member 1311b may include a lever longitudinal axis 1307b and a lever member portion 1304. Lever member portion 1302a and lever member portion 1304 include a first subset 1340a of engagement members and a second subset 1342 of engagement members, subset 1340a being disposed in a longitudinal distance, D, from subset 1342a. According to some examples, surgical instrument 1301 may facilitate a modification of a "Bonnie" forceps configuration.

In the example shown, subset 1340a of engagement members includes an engagement tooth 1310 associated with lever member portion 1302a and engagement teeth 1320a and 1320b associated with lever member portion 1304. By contrast, subset 1340b of engagement members is a converse arrangement of engagement members disposed in subset 1340a. For example, subset 1340a of engagement members includes engagement teeth 1315a and 1315b associated with lever member portion 1302a, and engagement tooth 1325 associated with lever member portion 1304. Cross-sectional views of engagement members of subsets 1340a and 1340b are depicted in subsets 1340b and 1342b, respectively.

According to some examples, engagement members in subsets 1340a and 1342a may be configured differently. To illustrate, consider that a lever member portion 1302b includes an engagement tooth 1310 having a proximal edge 1311 orthogonal to longitudinal axis 1307a and a distal edge 1312 at an angle ("1") 1333, whereas engagement teeth 1315, such as engagement tooth 1315a, may have a proximal edge 1313 at an angle ("2") 1335 and a distal edge 1314 orthogonal to longitudinal axis 1307a. Note that each subset of engagement members may include any number of engagement teeth, according to various examples.

Figure 14A:
FIGS. 14A, 14B, and 14C depict a front view, a side view, and an perspective view, respectively, of a first example of a surgical instrument, according to various examples.
Figure 14B:
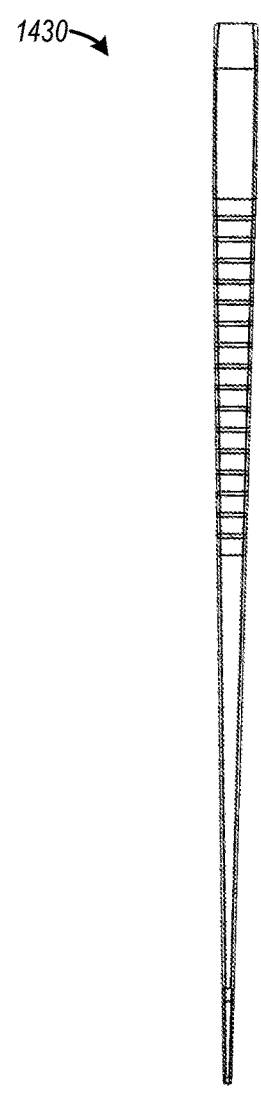
Figure 14C:
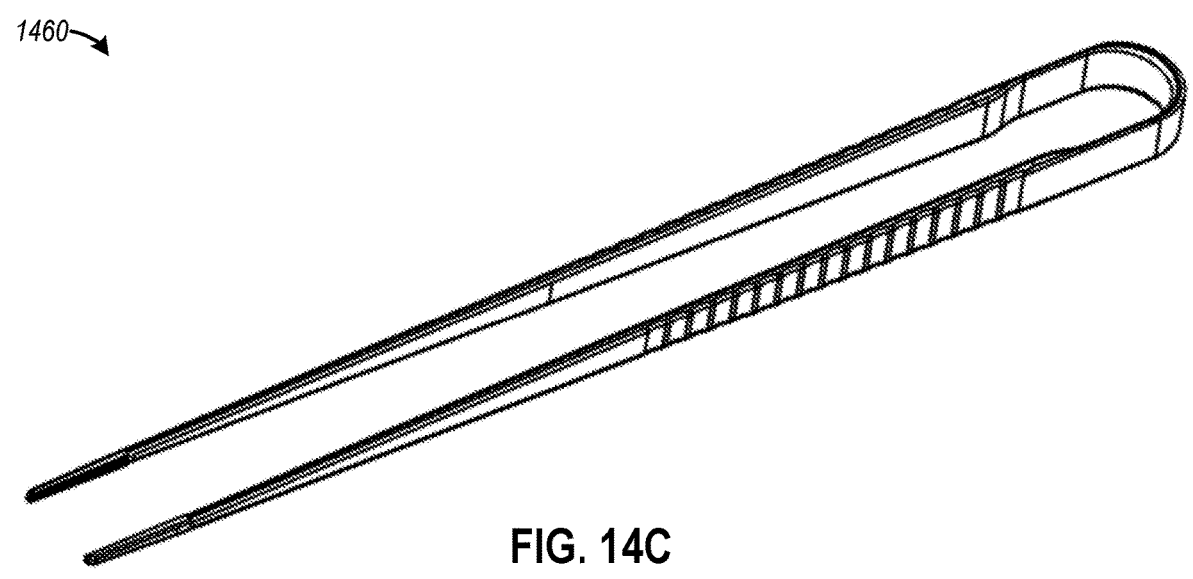

FIGS. 14A, 14B, and 14C depict a front view, a side view, and an perspective view, respectively, of a first example of a surgical instrument, according to various examples.

Figures 15A, 15B:
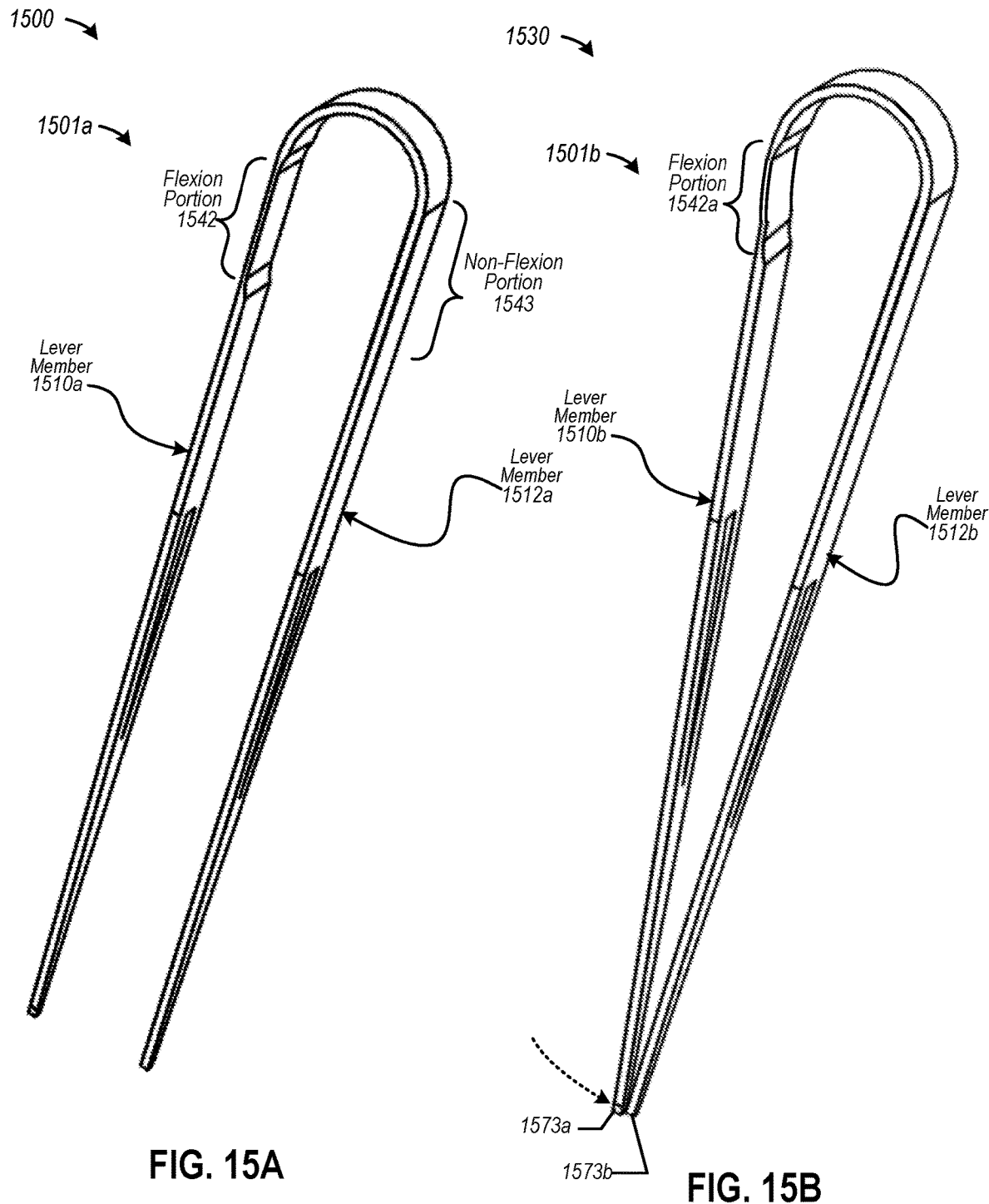
FIGS. 15A and 15B are diagrams depicting different states of a second example of a surgical instrument, according to some examples.

FIGS. 15A and 15B are diagrams depicting different states of a second example of a surgical instrument, according to some examples. Diagram 1500 of FIG. 15A depicts a surgical instrument 1501a in at least one open state. Surgical instrument 1501a includes a flexion portion 1542 associated with a lever member 1510a, and includes a non-flexion portion 1543 associated with a lever member 1512b. Diagram 1550 of FIG. 15B depicts a surgical instrument 1501b in at least one closed (or closing) state. Upon application of one or more applied forces to one or more lever members 1510b and 1512b, flexion portion 1542a may elastically deform or bend to facilitate rotation of end 1573a to end 1573b. In some cases, end 1573b may stationary (or substantially stationary), or may rotate at a rate less than that of end 1573a.

FIGS. 16A, 16B, and 16C depict a front view, a side view, and an perspective view, respectively, of another example of a surgical instrument, according to various examples.

Figure 17:
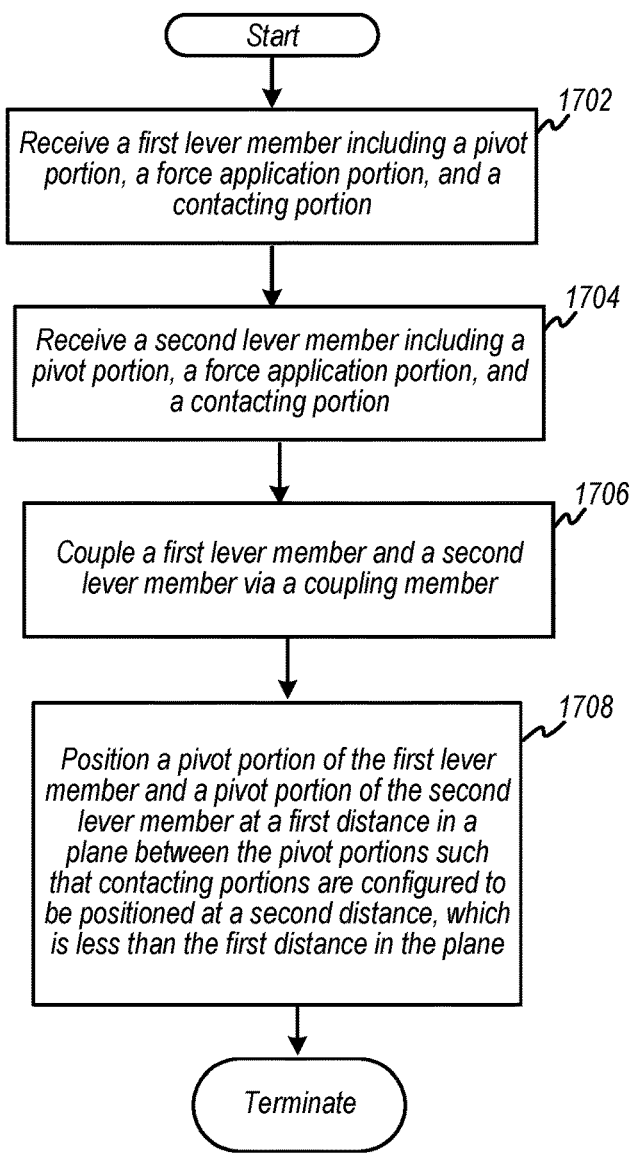
FIG. 17 is a diagram depicting an example of a flow to manufacture a surgical instrument, according to some examples.

FIG. 17 is a diagram depicting an example of a flow to manufacture a surgical instrument, according to some examples. At 1720, a first lever member including a pivot portion, a force application portion, and a contacting portion is received. At 1704, a second lever member including a pivot portion, a force application portion, and a contacting portion is received. At 1706, a first lever member and a second lever member coupled to each other via a coupling member, each of which may be formed together as using a monolithic material, or may be integrated together. At 1708, a pivot portion of a first lever member and a pivot portion of a second lever member may be positioned at a first distance in a plane from each other. Further, surgical instrument may be configured to rotate one or more contacting portions to a second distance from each other. The second distance may be less than the first distance in the plane.

In view of the foregoing, the structures and/or functionalities depicted in FIGS. 3 and 4 as well as other description and figures described herein, describe a surgical instrument implementing a coupling member that provides for multiple pivot axes displaced from each other, according to some embodiments. According to various examples, surgical forceps implementing multiple pivot axes described herein may provide for one or more of (1) enhanced effective length with which to access a surgery site, (2) increased flexibility or ability to elastically deform to reduce applied forces, which, in turn, may reduce fatigue in a surgeon's hand, and (3) increased grip strength at the ends based on, for example, a wedge configuration formed among multiple pivot axes and the ends or tips of lever members.

Displacement of pivot axes from each other may facilitate application of more pressure or closing forces at the ends of lever members of exemplary surgery forceps. Further, the displacement of pivot axes from each other also facilitates an ability to position a rotation axis at a proximal end of surgical forceps, thereby increasing an amount of usable or effective length than otherwise might be the case. In some non-limiting examples, an effective or useable length may be 25 to 40% more than otherwise might be the case. In various implementations, applied force portions of surgical forceps may be disposed on one side of a bisecting plane, the one side including a proximal end adjacent to multiple pivot axes.

In some examples, one or more flexion portions may be implement adjacent a proximal end of surgical forceps, which, in turn, may enhance its mechanical advantage. In addition, displacement of pivot axes and positioning of a rotation axis enables closure of lever members in a manner that provides a more ergonomic position to apply pressure or forces to surgical forceps, which, in turn, reduces fatigue to a surgeon.

In some examples, surgical forceps may be non-locking and non-pivoting, thereby omitting a pivot assembly, which may simplify manufacturing processes that may reduce costs. In some implementations, a first lever member, a second lever member, and a coupling member portion may be formed with a monolithic material as a monolithic, contiguous structure (e.g., a first lever member, a second lever member, and a coupling member portion may be formed in a single mold or from a single piece of material, such as stainless steel flat bar stock). Surgical forceps described herein may be formed using plastic materials, such as styrene, ABS, and polycarbonate, or any other medical-grade materials, etc.

Examples herein describe and depict various examples of locking elements and various examples of protective members with certain functionalities, orientations, structures, and configurations, all of which are merely exemplary and are not intended to limiting. Thus, various other functionalities, structures, orientations, and configurations of the structures described herein are within the scope of the present disclosure. Note, too, that various surgical tools described herein are applicable for performing surgery on any organism, including veterinary uses.

Note that the structures and constituent elements described herein, as well as their functionality, may be aggregated or combined with one or more other structures or elements. Alternatively, the elements and their functionality may be subdivided into constituent sub-elements, if any.

A detailed description of one or more examples has been provided above along with accompanying figures. The detailed description is provided in connection with such examples, but is not limited to any particular example. The scope is limited only by the claims, and numerous alternatives, modifications, and equivalents are encompassed. Numerous specific details are set forth in the following description in order to provide a thorough understanding. These details are provided as examples and the described techniques may be practiced according to the claims without some or all of the accompanying details. For clarity, technical material that is known in the technical fields related to the examples has not been described in detail to avoid unnecessarily obscuring the description.

The description, for purposes of explanation, uses specific nomenclature to provide a thorough understanding of the various embodiments. However, it will be apparent that specific details are not required in order to practice the various embodiments. In fact, this description should not be read to limit any feature or aspect of to any embodiment; rather features and aspects of one example can readily be interchanged with other examples. Notably, not every benefit described herein need be realized by each example of the various embodiments; rather any specific example may provide one or more of the advantages discussed above. In the claims, elements and/or operations do not imply any particular order of operation, unless explicitly stated in the claims. It is intended that the following claims and their equivalents define the scope of the various embodiments.

What is claimed:

1. A surgical instrument comprising:
a first lever member including:
a first pivot portion about which the first lever member is rotatable in a plane, the first pivot portion including a first flexion portion,
a first contacting portion associated with a distal end, and
at least a portion of the first lever member being configured to include a first lever longitudinal axis that extends from the first pivot portion to the first contacting portion, and further being configured to include at least a portion of surface treatment between a proximal end and a bisecting plane;
a second lever member including:
a second pivot portion about which the second lever member is rotatable in the plane, the second pivot portion including a second flexion portion, wherein the first flexion portion and the second flexion portion are dimensioned to have widths less than other portions of the first and the second lever members, the widths being dimensioned relative to the plane in which the first lever member and the second lever member rotate,
a second contacting portion associated with the distal end, and
at least a portion of the second lever member being configured to include a second lever longitudinal axis that extends from the second pivot portion to the second contacting portion, and further being configured to include at least a portion of surface treatment between the proximal end and the bisecting plane; and
a coupling member associated with the proximal end configured to couple the first lever member to the second lever member, and further configured to position the first pivot portion of the first lever member at a first distance relative to the second pivot portion of the second lever member,
wherein the first lever member and the second lever member are configured to receive one or more first applied forces in association with one or more of the portions of the surface treatment between the proximal end and the bisecting plane to translate the first contacting portion and the second contacting portion into at least a first closing state in which the first contacting portion is positioned at a second distance relative to the second contacting portion to impart the one or more first applied forces relative to the first and the second contacting portions, the second distance being less than the first distance,
wherein the first lever member and the second lever member are further configured to receive one or more second applied forces in association with the one or more of the portions of the surface treatment to translate the first contacting portion and the second contacting portion into at least a second closing state in which a first adjacent portion of the first lever member adjacent the first contacting portion is positioned relative to a second adjacent portion of the second lever member adjacent the second contacting portion, the first lever member and the second lever member configured to impart the one or more second applied forces at the first and the second contacting portions and at the first and the second adjacent portions in the second closing state.

2. The surgical instrument of claim 1, wherein the first lever member, the second lever member, and the coupling member are formed to include a metal material.

3. The surgical instrument of claim 1, wherein the first pivot portion and the second pivot portion each comprises:
a proximal section coupled to the coupling member; and
a distal section,
wherein, in the first closing state, the proximal section is positioned at a distance relative to a longitudinal plane that is equivalent to, or greater than, another distance between the distal section and the longitudinal plane.

4. The surgical instrument of claim 1, wherein the first lever member and the second lever member in the first closing state are configured to form a wedge configuration.

5. The surgical instrument of claim 1, wherein the first lever member and the second lever member are configured to form a wedge configuration that establishes a pinch distance between the first and the second lever members,
wherein the pinch distance decreases along the first lever member and the second lever member from the first distance between the first and the second pivot portions adjacent the proximal end to the first and the second contacting portions adjacent the distal end.

6. The surgical instrument of claim 1, wherein the first lever member and the second lever member are configured to form a wedge configuration comprising:
a first edge extending coextensive with the first lever member from the first pivot portion to a first point in the first contacting portion; and
a second edge extending coextensive with the second lever member from the second pivot portion to a second point in the second contacting portion.

7. The surgical instrument of claim 6, wherein the wedge configuration comprises:
a first edge and a second edge, both of which include straight lines.

8. The surgical instrument of claim 1, wherein the first lever member and the second lever member in the first closing state are configured to form a wedge configuration having an outer edge associated with each of the first and the second lever members,
wherein the first and the second lever members are configured to receive the one or more first applied forces and the one or more second applied forces at any point along the outer edge of the wedge configuration.

9. The surgical instrument of claim 1, wherein the first lever member and the second lever member are configured to form a wedge configuration to receive a lift force that intercepts a surface of one or more of the first lever member and the second lever member associated with the wedge configuration,
wherein the lift force is a force component parallel to a longitudinal plane.

10. The surgical instrument of claim 1, wherein the first pivot portion, the second pivot portion, the first contacting portion, and the second contacting portion comprise:
a first pivot axis, a second pivot axis, a first distal end, and a second distal end, respectively,
wherein the first lever longitudinal axis extends between the first pivot axis and the first distal end, and the second lever longitudinal axis extends between the second pivot axis and the second distal end.

11. The surgical instrument of claim 1, wherein the first pivot portion and the second pivot portion comprise:
the first flexion portion and the second flexion portion,
wherein the first lever longitudinal axis extends from the first flexion portion to at least the first contacting portion, and the second lever longitudinal axis extends from the second flexion portion to at least the second contacting portion.

12. The surgical instrument of claim 1, wherein the one or more second applied forces are greater in magnitude than of the one or more first applied forces,
wherein the one or more second applied forces are configured to cause portions of the first and the second level member adjacent the first and the second contacting portions to contact.

13. The surgical instrument of claim 1, wherein at least one of the first lever longitudinal axis and the second lever longitudinal axis is a line passing length-wise through at least a portion of at least one of the first lever and the second members.

14. The surgical instrument of claim 1, wherein at least a portion of either the first lever member or the second lever member, or both, has a shape extending along a lever longitudinal axis from a pivot portion to a contacting portion.

15. The surgical instrument of claim 14, wherein the shape comprises:
a straight shape.

16. The surgical instrument of claim 1, wherein the coupling member comprises:
an outer coupling member.

17. The surgical instrument of claim 16, further comprising:
a proximal end of the surgical instrument that includes a rotation axis at which the first lever member couples to the second lever member; and
distal ends of the surgical instrument,
wherein a length of the surgical instrument extends from the rotational axis at the proximal end to the distal ends.

18. A surgical instrument comprising:
a first lever member including a first flexion portion disposed adjacent to a proximal end including a first pivot axis about which the first lever member is rotatable in a plane, the first lever member further including a first force application portion and a first contacting portion, the first lever member including a metal material and further including at least a portion of surface treatment between a portion of the proximal end and a bisecting plane;
a second lever member including a second flexion portion disposed adjacent to the proximal end including a second pivot axis about which the second lever member is rotatable in the plane, the second lever member further including a second force application portion and a second contacting portion, the second lever member including the metal material, and further including at least a portion of surface treatment between the proximal end and the bisecting plane, wherein the first flexion portion and the second flexion portion are dimensioned to have widths less than other portions of the first and the second lever members, the widths being dimensioned relative to the plane in which the first lever member and the second lever member rotate;
one or more longitudinal subsets of teeth in which subset of teeth are arranged longitudinally in the first contacting portion and the second contacting portion adjacent to a distal end, the one or more longitudinal subsets of teeth including the metal material; and an outer coupling member configured to couple the first lever member to the second lever member adjacent to the proximal end, and further configured to position the first pivot axis of the first lever member and the second pivot axis of the second lever member at a first distance between the first pivot axis and the second pivot axis, the outer coupling member including the metal material, wherein each of the first lever member and the second lever member are configured to receive a first applied force at one or more portions of the surface treatment between the proximal end and the bisecting plane to position the first and the second contacting portions to a first closed state at a second distance to impart the first applied force at the first and the second contacting portions, the second distance being less than the first distance, the first and the second contacting portions being positioned to impart the first applied force at the first and the second contacting portions in the first closed state, wherein each of the first lever member and the second lever member are further configured to receive a second applied force at the one or more of the portions of the surface treatment to position the first and the second contacting portions to a second closed state in which a first adjacent portion of the first lever member adjacent the first contacting portion is positioned relative to a second adjacent portion of the second lever member adjacent the second contacting portion, the first lever member and the second lever member configured to impart in the second closed state the second applied force at the first and the second contacting portions and at the first and the second adjacent portions, wherein a pinch distance between the first and the second lever members decreases from the first distance between the first and the second pivot portions to the one or more longitudinal subsets of teeth.

19. The surgical instrument of claim 18, wherein the first lever member and the second lever member are configured to translate the first contacting portion and the second contacting portion into an open state in absence of the one or more applied forces, the first lever member including a first lever longitudinal axis and the second lever member including a second lever longitudinal axis, wherein in the open state the first lever longitudinal axis and the second lever longitudinal axis are in a parallel configuration.

20. A method to manufacture a surgical instrument, the method comprising:

forming a first lever member including a first flexion portion including a first pivot portion about which the first lever member is rotatable in a plane, the first lever member further including a first contacting portion associated with a distal end, and at least a portion of the first lever member being configured to include a first lever longitudinal axis that extends from the first pivot portion to the first contacting portion, the first lever member including at least a portion of surface treatment between a proximal end and a bisecting plane;

forming a second lever member including a second flexion portion including a second pivot portion about which the second lever member is rotatable in the plane, the second lever member further including a second contacting portion associated with the distal end, and at least a portion of the second lever member being configure to include a second lever longitudinal axis that extends from the second pivot portion to the second contacting portion, the second lever member including at least a portion of surface treatment between the proximal end and the bisecting plane, wherein the first flexion portion and the second flexion portion are dimensioned to have widths less than other portions of the first and the second lever members, the widths being dimensioned relative to the plane in which the first lever member and the second lever member rotate; and coupling the first lever member to the second lever member by forming a coupling member at the proximal end that is configured to position the first pivot portion of the first lever member at a first distance relative to the second pivot portion of the second lever member, wherein the first lever member and the second lever member are configured to receive at least one first applied force in association with one or more of the portions of the surface treatment between the proximal end and the bisecting plane to translate the first contacting portion and the second contacting portion into a first closing state in which the first contacting portion is positioned at a second distance relative to the second contacting portion to impart least one first applied force relative to the first and the second contacting portions, the second distance being less than the first distance, wherein the first lever member, the second lever member, and the coupling member are formed to include a metal material, wherein the first lever member and the second lever member are further configured to receive at least one second applied force in association with the one or more of the portions of the surface treatment to translate the first contacting portion and the second contacting portion into at a second closing state in which a first adjacent portion of the first lever member adjacent the first contacting portion is positioned relative to a second adjacent portion of the second lever member adjacent the second contacting portion, the first lever member and the second lever member configured to impart the one or more second applied forces at the first and the second contacting portions and at the first and the second adjacent portions in the second closing state.

* * * * *